(12) United States Patent
Chobotov et al.

(10) Patent No.: US 7,147,661 B2
(45) Date of Patent: Dec. 12, 2006

(54) RADIALLY EXPANDABLE STENT

(75) Inventors: Michael V. Chobotov, Santa Rosa, CA (US); Brian Glynn, Santa Rosa, CA (US); Stuart Kari, Windsor, CA (US); Maurice Marthaler, Santa Rosa, CA (US); Robert Whirley, Santa Rosa, CA (US); Isaac Zacharias, Santa Rosa, CA (US)

(73) Assignee: Boston Scientific Santa Rosa Corp., Santa Rosa, CA (US)

( * ) Notice: Subject to any disclaimer, the term of this patent is extended or adjusted under 35 U.S.C. 154(b) by 0 days.

(21) Appl. No.: 10/029,559

(22) Filed: Dec. 20, 2001

(65) Prior Publication Data

US 2003/0120331 A1 Jun. 26, 2003

(51) Int. Cl.
*A61F 2/06* (2006.01)
(52) U.S. Cl. ............ 623/1.16; 623/1.14; 623/1.25
(58) Field of Classification Search ........... 623/1.13, 623/1.14, 1.25, 23.67, 1.35, 1.36, 1.15, 1.16
See application file for complete search history.

(56) References Cited

U.S. PATENT DOCUMENTS

| | | | |
|---|---|---|---|
| 3,540,431 A | 11/1970 | Uddin | |
| 3,631,854 A | 1/1972 | Fryer | |
| 3,818,511 A | 6/1974 | Goldberg et al. | |
| 3,900,027 A | 8/1975 | Keedwell | |
| 3,902,198 A | 9/1975 | Rathjen | |
| 3,991,767 A | 11/1976 | Miller, Jr. et al. | |
| 4,140,126 A | 2/1979 | Choudhury | |
| 4,183,102 A | 1/1980 | Guiset | |
| 4,187,390 A | 2/1980 | Gore | |
| 4,208,745 A | 6/1980 | Okita | |
| 4,214,587 A | 7/1980 | Sakura | |
| 4,459,252 A | 7/1984 | MacGregor | |
| 4,474,630 A | 10/1984 | Planck et al. | |
| 4,497,074 A | 2/1985 | Rey et al. | |
| 4,512,338 A | 4/1985 | Balko et al. | |
| 4,550,447 A | 11/1985 | Seiler, Jr. et al. | |
| 4,552,707 A | 11/1985 | How | |
| 4,562,596 A | 1/1986 | Kornberg | |
| 4,580,568 A | 4/1986 | Gianturco | |
| 4,592,754 A | 6/1986 | Gupte et al. | |
| 4,617,932 A | 10/1986 | Kornberg | |
| 4,647,416 A | 3/1987 | Seiler, Jr. et al. | |

(Continued)

FOREIGN PATENT DOCUMENTS

EP 0 407 566 A1 1/1990

(Continued)

OTHER PUBLICATIONS

Haimovitch, L. and Patterson, N., "Robust growth is forecast for endovascular repair of AAAs," The BBI Newsletter, vol. 26, No. 5, pp. 113-144, (May 2003).

(Continued)

*Primary Examiner*—Paul B. Prebilic
(74) *Attorney, Agent, or Firm*—Hoffmann & Baron, LLP

(57) ABSTRACT

This invention is a system for the treatment of body passageways; in particular, vessels with vascular disease. The system includes an endovascular graft with a low-profile delivery configuration and a deployed configuration in which it conforms to the morphology of the vessel or body passageway to be treated as well as various connector members and stents. The graft is made from an inflatable graft body section and may be bifurcated. One or more inflatable cuffs may be disposed at either end of the graft body section. At least one inflatable channel is disposed between and in fluid communication with the inflatable cuffs.

19 Claims, 14 Drawing Sheets

U.S. PATENT DOCUMENTS

| | | |
|---|---|---|
| 4,655,771 A | 4/1987 | Wallsten |
| 4,665,906 A | 5/1987 | Jervis |
| 4,705,517 A | 11/1987 | DiPisa, Jr. |
| 4,739,762 A | 4/1988 | Palmaz |
| 4,776,337 A | 10/1988 | Palmaz |
| 4,787,899 A | 11/1988 | Lazarus |
| 4,816,028 A | 3/1989 | Kapadia et al. |
| 4,830,003 A | 5/1989 | Wolff et al. |
| 4,856,516 A | 8/1989 | Hillstead |
| 4,941,870 A | 7/1990 | Okada et al. |
| 4,955,899 A | 9/1990 | Corna et al. |
| 4,957,669 A | 9/1990 | Primm |
| 5,019,090 A | 5/1991 | Pinchuk |
| 5,064,435 A | 11/1991 | Porter |
| 5,100,422 A | 3/1992 | Berguer et al. |
| 5,104,399 A | 4/1992 | Lazarus |
| 5,104,400 A | 4/1992 | Berguer et al. |
| 5,108,424 A | 4/1992 | Hoffman, Jr. et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,139,480 A | 8/1992 | Hickle et al. |
| 5,151,105 A | 9/1992 | Kwan-Gett |
| 5,156,620 A | 10/1992 | Pigott |
| 5,171,252 A | 12/1992 | Friedland |
| 5,171,262 A | 12/1992 | MacGregor |
| 5,195,984 A | 3/1993 | Schatz |
| 5,197,978 A | 3/1993 | Hess |
| 5,207,695 A * | 5/1993 | Trout, III .................. 623/1.36 |
| 5,217,483 A | 6/1993 | Tower |
| 5,219,355 A | 6/1993 | Parodi et al. |
| 5,226,913 A | 7/1993 | Pinchuk |
| 5,234,447 A | 8/1993 | Kaster et al. |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,330,528 A | 7/1994 | Lazim |
| 5,344,426 A | 9/1994 | Lau et al. |
| 5,344,444 A | 9/1994 | Glastra |
| 5,354,310 A | 10/1994 | Garnic et al. |
| 5,360,443 A | 11/1994 | Barone et al. |
| 5,366,504 A | 11/1994 | Andersen et al. |
| 5,370,682 A | 12/1994 | Schmitt |
| 5,370,691 A | 12/1994 | Samson |
| 5,387,235 A | 2/1995 | Chuter |
| 5,397,345 A | 3/1995 | Lazarus et al. |
| 5,397,355 A * | 3/1995 | Marin et al. ................. 623/1.2 |
| 5,405,379 A | 4/1995 | Lane |
| 5,411,550 A | 5/1995 | Herweck et al. |
| 5,423,851 A | 6/1995 | Samuels |
| 5,443,498 A | 8/1995 | Fontaine |
| 5,456,713 A | 10/1995 | Chuter |
| 5,464,419 A | 11/1995 | Glastra |
| 5,464,449 A | 11/1995 | Ryan et al. |
| 5,480,423 A | 1/1996 | Ravenscroft et al. |
| 5,489,295 A * | 2/1996 | Piplani et al. ............ 623/1.35 |
| 5,507,769 A | 4/1996 | Marin et al. |
| 5,507,770 A | 4/1996 | Turk |
| 5,522,880 A | 6/1996 | Barone et al. |
| 5,527,353 A | 6/1996 | Schmitt |
| 5,527,355 A | 6/1996 | Ahn |
| 5,529,653 A | 6/1996 | Glastra |
| 5,534,024 A | 7/1996 | Rogers et al. |
| 5,536,274 A | 7/1996 | Neuss |
| 5,554,180 A | 9/1996 | Turk |
| 5,554,181 A | 9/1996 | Das |
| 5,562,724 A | 10/1996 | Vorwerk et al. |
| 5,562,726 A * | 10/1996 | Chuter ...................... 623/1.35 |
| 5,562,728 A | 10/1996 | Lazarus et al. |
| 5,571,079 A | 11/1996 | Bello et al. |
| 5,571,173 A | 11/1996 | Parodi |
| 5,575,817 A | 11/1996 | Martin |
| 5,578,071 A | 11/1996 | Parodi |
| 5,578,072 A | 11/1996 | Barone et al. |
| 5,591,197 A | 1/1997 | Orth et al. |
| 5,591,229 A | 1/1997 | Parodi |
| 5,607,468 A | 3/1997 | Rogers et al. |
| 5,607,478 A | 3/1997 | Lentz et al. |
| 5,609,624 A | 3/1997 | Kalis |
| 5,609,625 A | 3/1997 | Piplani et al. |
| 5,609,628 A | 3/1997 | Keranen |
| 5,618,301 A | 4/1997 | Hauenstein et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A * | 5/1997 | Lauterjung ................. 623/1.15 |
| 5,632,772 A | 5/1997 | Alcime et al. |
| 5,632,840 A | 5/1997 | Campbell |
| 5,653,746 A | 8/1997 | Schmitt |
| 5,662,675 A | 9/1997 | Polanskyj Stockert |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A * | 10/1997 | Orth et al. .................. 606/198 |
| 5,683,449 A | 11/1997 | Marcade |
| 5,683,451 A | 11/1997 | Lenker et al. |
| 5,683,453 A | 11/1997 | Palmaz |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,700,285 A | 12/1997 | Myers et al. |
| 5,707,378 A | 1/1998 | Ahn et al. |
| 5,709,701 A | 1/1998 | Parodi |
| 5,709,703 A | 1/1998 | Lukic et al. |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,733,325 A | 3/1998 | Robinson et al. |
| 5,735,892 A | 4/1998 | Myers et al. |
| 5,747,128 A | 5/1998 | Campbell et al. |
| 5,749,880 A | 5/1998 | Banas et al. |
| 5,749,920 A | 5/1998 | Quiachon et al. |
| 5,755,776 A | 5/1998 | Al-Saadon |
| 5,769,887 A | 6/1998 | Brown et al. |
| 5,780,807 A | 7/1998 | Saunders |
| 5,785,679 A | 7/1998 | Abolfathi et al. |
| 5,788,626 A | 8/1998 | Thompson |
| 5,789,047 A | 8/1998 | Sasaki et al. |
| 5,800,508 A | 9/1998 | Goicoechea et al. |
| 5,800,512 A | 9/1998 | Lentz et al. |
| 5,800,518 A | 9/1998 | Piplani et al. |
| 5,824,039 A | 10/1998 | Piplani et al. |
| 5,824,044 A | 10/1998 | Quiachon et al. |
| 5,827,320 A | 10/1998 | Richter et al. |
| 5,836,966 A | 11/1998 | St. Germain |
| 5,843,158 A | 12/1998 | Lenker et al. |

| Patent No. | Date | Inventor |
|---|---|---|
| 5,843,160 A | 12/1998 | Rhodes |
| 5,843,164 A | 12/1998 | Frantzen et al. |
| 5,843,167 A | 12/1998 | Dwyer et al. |
| 5,843,170 A | 12/1998 | Ahn |
| 5,853,419 A | 12/1998 | Imran |
| 5,855,598 A | 1/1999 | Pinchuk |
| 5,861,027 A | 1/1999 | Trapp |
| 5,871,536 A | 2/1999 | Lazarus |
| 5,871,537 A | 2/1999 | Holman et al. |
| 5,873,906 A | 2/1999 | Lau et al. |
| 5,876,432 A | 3/1999 | Lau et al. |
| 5,906,641 A | 5/1999 | Thompson et al. |
| 5,911,754 A | 6/1999 | Kanesaka et al. |
| 5,922,020 A | 7/1999 | Klein et al. |
| 5,925,061 A | 7/1999 | Ogi et al. |
| 5,926,650 A | 7/1999 | Suzuki et al. |
| 5,961,545 A | 10/1999 | Lentz et al. |
| 5,961,546 A | 10/1999 | Robinson et al. |
| 5,968,090 A | 10/1999 | Ratcliff et al. |
| 5,972,441 A | 10/1999 | Campbell et al. |
| 5,976,179 A | 11/1999 | Inoue |
| 5,976,650 A | 11/1999 | Campbell et al. |
| 5,984,956 A | 11/1999 | Tweden et al. |
| 5,989,287 A | 11/1999 | Yang et al. |
| 5,993,481 A | 11/1999 | Marcade et al. |
| 5,997,573 A | 12/1999 | Quijano et al. |
| 6,001,123 A | 12/1999 | Lau |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,017,362 A | 1/2000 | Lau |
| 6,017,364 A | 1/2000 | Lazarus |
| 6,019,787 A | 2/2000 | Richard et al. |
| 6,025,044 A | 2/2000 | Campbell et al. |
| 6,027,811 A | 2/2000 | Campbell et al. |
| 6,030,415 A | 2/2000 | Chuter |
| 6,036,702 A | 3/2000 | Bachinski et al. |
| 6,036,723 A | 3/2000 | Anidjar et al. |
| 6,039,755 A | 3/2000 | Edwin et al. |
| 6,042,605 A | 3/2000 | Martin et al. |
| 6,042,606 A | 3/2000 | Frantzen |
| 6,051,020 A | 4/2000 | Goicoechea et al. |
| 6,053,943 A | 4/2000 | Edwin et al. |
| 6,059,823 A | 5/2000 | Holman et al. |
| 6,063,114 A | 5/2000 | Nash et al. |
| 6,077,296 A | 6/2000 | Shokoohi et al. |
| 6,090,128 A | 7/2000 | Douglas |
| 6,098,630 A | 8/2000 | Papazoglou |
| 6,102,938 A | 8/2000 | Evans et al. |
| 6,102,940 A | 8/2000 | Robichon et al. |
| 6,110,198 A | 8/2000 | Fogarty et al. |
| 6,113,628 A | 9/2000 | Borghi |
| 6,124,523 A | 9/2000 | Banas et al. |
| 6,126,685 A | 10/2000 | Lenker et al. |
| 6,129,756 A | 10/2000 | Kugler et al. |
| 6,132,459 A | 10/2000 | Piplani et al. |
| 6,139,572 A | 10/2000 | Campbell et al. |
| 6,143,015 A | 11/2000 | Nobles |
| 6,146,416 A | 11/2000 | Andersen et al. |
| 6,146,417 A | 11/2000 | Ischinger |
| 6,149,665 A | 11/2000 | Gabbay |
| 6,149,682 A | 11/2000 | Frid |
| 6,152,956 A | 11/2000 | Pierce |
| 6,153,292 A | 11/2000 | Bell et al. |
| 6,156,063 A | 12/2000 | Douglas |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,174,326 B1 | 1/2001 | Kitaoka et al. |
| 6,183,504 B1 | 2/2001 | Inoue |
| 6,187,036 B1 | 2/2001 | Shaolian et al. |
| 6,193,745 B1 | 2/2001 | Fogarty et al. |
| 6,197,049 B1 | 3/2001 | Shaolian et al. |
| 6,203,568 B1 | 3/2001 | Lombardi et al. |
| 6,203,569 B1 | 3/2001 | Wijay |
| 6,210,435 B1 | 4/2001 | Piplani et al. |
| 6,217,608 B1 | 4/2001 | Penn et al. |
| 6,221,102 B1 | 4/2001 | Baker et al. |
| 6,235,050 B1 | 5/2001 | Quiachon et al. |
| 6,238,432 B1 | 5/2001 | Parodi |
| 6,245,097 B1 | 6/2001 | Inoue |
| 6,245,101 B1 * | 6/2001 | Drasler et al. ............ 623/1.15 |
| 6,245,102 B1 | 6/2001 | Jayaraman |
| 6,248,116 B1 | 6/2001 | Chevillon et al. |
| 6,251,133 B1 | 6/2001 | Richter et al. |
| 6,254,632 B1 * | 7/2001 | Wu et al. .................. 623/1.15 |
| 6,258,114 B1 | 7/2001 | Konya et al. |
| 6,258,116 B1 | 7/2001 | Hojeibane |
| 6,264,684 B1 | 7/2001 | Banas et al. |
| 6,273,910 B1 | 8/2001 | Limon |
| 6,273,911 B1 | 8/2001 | Cox et al. |
| 6,280,466 B1 | 8/2001 | Kugler et al. |
| 6,283,991 B1 | 9/2001 | Cox et al. |
| 6,287,330 B1 | 9/2001 | Johansson et al. |
| 6,287,335 B1 * | 9/2001 | Drasler et al. ............ 623/1.28 |
| 6,287,336 B1 | 9/2001 | Globerman et al. |
| 6,293,968 B1 | 9/2001 | Taheri |
| 6,293,969 B1 | 9/2001 | Chuter |
| 6,296,661 B1 | 10/2001 | Davila et al. |
| 6,302,908 B1 | 10/2001 | Parodi |
| 6,312,462 B1 * | 11/2001 | McDermott et al. ....... 623/1.25 |
| 6,315,791 B1 | 11/2001 | Gingras et al. |
| 6,319,276 B1 * | 11/2001 | Holman et al. ............ 623/1.11 |
| 6,319,278 B1 | 11/2001 | Quinn |
| 6,325,819 B1 | 12/2001 | Pavcnik et al. |
| 6,325,823 B1 | 12/2001 | Horzewski et al. |
| 6,325,825 B1 | 12/2001 | Kula et al. |
| 6,331,188 B1 | 12/2001 | Lau et al. |
| 6,331,189 B1 | 12/2001 | Wolinsky et al. |
| 6,331,190 B1 | 12/2001 | Shokoohi et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,348,065 B1 | 2/2002 | Brown et al. |
| 6,350,277 B1 | 2/2002 | Kocur |
| 6,352,553 B1 | 3/2002 | van der Burg et al. |
| 6,355,055 B1 | 3/2002 | Waksman et al. |
| 6,355,056 B1 | 3/2002 | Pnheiro |
| 6,368,355 B1 | 4/2002 | Uflacker |
| 6,379,382 B1 | 4/2002 | Yang |
| 6,387,124 B1 | 5/2002 | Buscemi et al. |
| 6,395,019 B1 * | 5/2002 | Chobotov .................. 623/1.13 |
| 6,398,803 B1 | 6/2002 | Layne et al. |
| 6,402,779 B1 | 6/2002 | Colone et al. |
| 6,406,489 B1 | 6/2002 | Richter et al. |
| 6,409,754 B1 | 6/2002 | Smith et al. |
| 6,409,756 B1 | 6/2002 | Murphy |
| 6,409,757 B1 | 6/2002 | Trout et al. |
| 6,416,538 B1 | 7/2002 | Ley et al. |
| 6,416,539 B1 | 7/2002 | Hassdenteufel |
| 6,423,084 B1 | 7/2002 | St. Germain |
| 6,423,089 B1 | 7/2002 | Gingras et al. |
| 6,423,090 B1 | 7/2002 | Hancock |
| 6,428,506 B1 | 8/2002 | Simhambhatla et al. |
| 6,428,565 B1 | 8/2002 | Wisselink |

| Patent No. | Date | Name |
|---|---|---|
| 6,428,569 B1 | 8/2002 | Brown |
| 6,428,570 B1 | 8/2002 | Globerman |
| 6,432,131 B1 | 8/2002 | Ravenscroft |
| 6,432,132 B1 | 8/2002 | Cottone et al. |
| 6,436,104 B1 | 8/2002 | Hojeibane |
| 6,436,133 B1 | 8/2002 | Furst et al. |
| 6,440,165 B1 | 8/2002 | Richter et al. |
| 6,443,981 B1 | 9/2002 | Colone et al. |
| 6,451,050 B1 | 9/2002 | Rudakov et al. |
| 6,451,053 B1 | 9/2002 | Dehdashtian et al. |
| 6,454,795 B1 | 9/2002 | Chuter |
| 6,454,796 B1 | 9/2002 | Barkman et al. |
| 6,461,381 B1 | 10/2002 | Israel et al. |
| 6,464,720 B1 | 10/2002 | Boatman et al. |
| 6,471,720 B1 | 10/2002 | Ehr et al. |
| 6,471,721 B1 | 10/2002 | Dang |
| 6,475,236 B1 | 11/2002 | Roubin et al. |
| 6,475,238 B1 | 11/2002 | Fedida |
| 6,478,815 B1 | 11/2002 | Alt |
| 6,478,816 B1 | 11/2002 | Kveen et al. |
| 6,482,166 B1 | 11/2002 | Fariabi |
| 6,482,227 B1 | 11/2002 | Solovay |
| 6,485,507 B1 | 11/2002 | Walak et al. |
| 6,485,508 B1 | 11/2002 | McGuinness |
| 6,485,509 B1 | 11/2002 | Killion et al. |
| 6,485,513 B1 | 11/2002 | Fan |
| 6,488,694 B1 | 12/2002 | Lau et al. |
| 6,488,701 B1 | 12/2002 | Nolting et al. |
| 6,488,705 B1 | 12/2002 | Schmitt et al. |
| 6,491,718 B1 | 12/2002 | Ahmad |
| 6,491,719 B1 | 12/2002 | Fogary et al. |
| 6,494,904 B1 | 12/2002 | Love |
| 6,494,907 B1 | 12/2002 | Bulver |
| 6,494,909 B1 | 12/2002 | Greenhalgh |
| 6,497,722 B1 | 12/2002 | Oepen et al. |
| 6,497,723 B1 | 12/2002 | Starck et al. |
| 6,500,203 B1 | 12/2002 | Thompson et al. |
| 6,500,204 B1 | 12/2002 | Igaki |
| 6,503,271 B1 | 1/2003 | Duerig et al. |
| 6,506,211 B1 | 1/2003 | Skubitz et al. |
| 6,508,834 B1 | 1/2003 | Pinchasik et al. |
| 6,517,571 B1 | 2/2003 | Brauker et al. |
| 6,517,573 B1 * | 2/2003 | Pollock et al. ............ 623/1.15 |
| 6,517,574 B1 | 2/2003 | Chuter |
| 6,520,984 B1 | 2/2003 | Garrison et al. |
| 6,524,335 B1 | 2/2003 | Hartley et al. |
| 6,533,811 B1 | 3/2003 | Ryan et al. |
| 6,537,202 B1 | 3/2003 | Frantzon |
| 6,540,778 B1 | 4/2003 | Quiachon et al. |
| 6,547,817 B1 | 4/2003 | Fischell et al. |
| 6,554,858 B1 | 4/2003 | Dereume et al. |
| 6,558,414 B1 | 5/2003 | Layne |
| 6,582,458 B1 | 6/2003 | White et al. |
| 6,652,570 B1 | 11/2003 | Smith et al. |
| 6,669,720 B1 | 12/2003 | Pierce |
| 2001/0004705 A1 | 6/2001 | Killion et al. |
| 2001/0004706 A1 | 6/2001 | Hojeibane |
| 2001/0007955 A1 | 7/2001 | Drasler et al. |
| 2001/0010013 A1 | 7/2001 | Cox et al. |
| 2001/0011188 A1 | 8/2001 | Berry et al. |
| 2001/0014823 A1 | 8/2001 | Ressemann et al. |
| 2001/0016770 A1 | 8/2001 | Allen et al. |
| 2001/0018610 A1 | 8/2001 | Limon |
| 2001/0020184 A1 | 9/2001 | Dehdashtian et al. |
| 2001/0023370 A1 | 9/2001 | Smith et al. |
| 2001/0027338 A1 | 10/2001 | Greenberg |
| 2001/0027339 A1 | 10/2001 | Boatman et al. |
| 2001/0029349 A1 | 10/2001 | Leschinsky |
| 2001/0029397 A1 | 10/2001 | Thompson |
| 2001/0037142 A1 | 11/2001 | Stelter et al. |
| 2001/0037146 A1 | 11/2001 | Lau et al. |
| 2001/0037147 A1 | 11/2001 | Lau et al. |
| 2001/0039446 A1 | 11/2001 | Edwin et al. |
| 2001/0041928 A1 | 11/2001 | Pavenik et al. |
| 2001/0044652 A1 | 11/2001 | Moore |
| 2001/0047198 A1 | 11/2001 | Drasler et al. |
| 2001/0049534 A1 | 12/2001 | Lachat |
| 2001/0049550 A1 | 12/2001 | Martin et al. |
| 2001/0053929 A1 | 12/2001 | Vonesh et al. |
| 2002/0002397 A1 | 1/2002 | Martin et al. |
| 2002/0007193 A1 | 1/2002 | Tanner et al. |
| 2002/0007212 A1 | 1/2002 | Brown et al. |
| 2002/0016623 A1 | 2/2002 | Kula et al. |
| 2002/0016626 A1 | 2/2002 | DiMatteo et al. |
| 2002/0016627 A1 | 2/2002 | Golds |
| 2002/0019665 A1 | 2/2002 | Dehdashtian et al. |
| 2002/0026231 A1 | 2/2002 | Shannon et al. |
| 2002/0032408 A1 | 3/2002 | Parker et al. |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0042645 A1 | 4/2002 | Shannon |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052645 A1 | 5/2002 | Kugler et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0091440 A1 | 7/2002 | Calcote |
| 2002/0095208 A1 | 7/2002 | Gregorich et al. |
| 2002/0096252 A1 | 7/2002 | Lukic |
| 2002/0098278 A1 | 7/2002 | Bates et al. |
| 2002/0099406 A1 | 7/2002 | Germain |
| 2002/0099436 A1 | 7/2002 | Thornton et al. |
| 2002/0099437 A1 | 7/2002 | Anson et al. |
| 2002/0107561 A1 | 8/2002 | Pinheiro |
| 2002/0111633 A1 | 8/2002 | Stoltze et al. |
| 2002/0111665 A1 | 8/2002 | Lauterjung |
| 2002/0111669 A1 | 8/2002 | Pazienza et al. |
| 2002/0116047 A1 | 8/2002 | Vardi et al. |
| 2002/0116048 A1 * | 8/2002 | Chobotov .................. 623/1.13 |
| 2002/0116051 A1 | 8/2002 | Cragg |
| 2002/0120321 A1 | 8/2002 | Gunderson et al. |
| 2002/0120327 A1 | 8/2002 | Cox et al. |
| 2002/0121497 A1 | 9/2002 | Tomonto |
| 2002/0123790 A1 | 9/2002 | White et al. |
| 2002/0123791 A1 | 9/2002 | Harrison |
| 2002/0123792 A1 | 9/2002 | Burgermeister |
| 2002/0123796 A1 | 9/2002 | Majercak et al. |
| 2002/0123797 A1 | 9/2002 | Majercak |
| 2002/0123798 A1 | 9/2002 | Burgermeister |
| 2002/0123799 A1 | 9/2002 | Burgermeister |
| 2002/0128703 A1 | 9/2002 | Ravenscroft |
| 2002/0128706 A1 | 9/2002 | Osypka |
| 2002/0133221 A1 | 9/2002 | Schatz |
| 2002/0138048 A1 | 9/2002 | Tuch |
| 2002/0138126 A1 | 9/2002 | Camrud et al. |
| 2002/0138129 A1 | 9/2002 | Armstrong et al. |
| 2002/0143381 A1 | 10/2002 | Gilligan et al. |
| 2002/0143386 A1 | 10/2002 | Davila et al. |
| 2002/0147489 A1 | 10/2002 | Hong et al. |
| 2002/0147493 A1 | 10/2002 | Doran et al. |
| 2002/0151954 A1 | 10/2002 | Brenneman |
| 2002/0151959 A1 | 10/2002 | Oepen |
| 2002/0151963 A1 | 10/2002 | Brian et al. |
| 2002/0156518 A1 | 10/2002 | Tehrani |
| 2002/0156521 A1 | 10/2002 | Ryan et al. |
| 2002/0156522 A1 | 10/2002 | Ivancev et al. |

| | | | | | | |
|---|---|---|---|---|---|---|
| 2002/0165602 A1 | 11/2002 | Douglas et al. | | EP | 1 212 989 A2 | 6/2002 |
| 2002/0165603 A1 | 11/2002 | Thornton et al. | | EP | 1 212 991 A2 | 6/2002 |
| 2002/0165607 A1 | 11/2002 | Alt | | EP | 0 877 582 B1 | 10/2002 |
| 2002/0169498 A1 | 11/2002 | Kim et al. | | EP | 1 266 636 A2 | 12/2002 |
| 2002/0169499 A1 | 11/2002 | Zilla et al. | | EP | 0 712 614 B1 | 4/2003 |
| 2002/0173836 A1 | 11/2002 | Pinchuk | | EP | 1 148 843 B1 | 4/2003 |
| 2002/0173837 A1 | 11/2002 | Lauterjung | | JP | 5161665 | 6/1993 |
| 2002/0173840 A1 | 11/2002 | Brucker et al. | | WO | 90/08801 A1 | 8/1990 |
| 2002/0177893 A1 | 11/2002 | Brown et al. | | WO | 90/14055 | 11/1990 |
| 2002/0183828 A1 | 12/2002 | Park et al. | | WO | 92/22604 A1 | 12/1992 |
| 2002/0183831 A1 | 12/2002 | Rolando et al. | | WO | 93/13824 | 7/1993 |
| 2002/0183832 A1 | 12/2002 | Penn et al. | | WO | 93/19804 | 10/1993 |
| 2002/0188341 A1 | 12/2002 | Elliott | | WO | 94/03127 | 2/1994 |
| 2002/0188346 A1 | 12/2002 | Healy et al. | | WO | 95/03754 | 2/1995 |
| 2002/0188347 A1 | 12/2002 | Mathis | | WO | 95/09585 | 4/1995 |
| 2002/0193862 A1 | 12/2002 | Mitelberg et al. | | WO | 95/09586 | 4/1995 |
| 2002/0193864 A1 | 12/2002 | Khosravi et al. | | WO | 95/11720 | 5/1995 |
| 2002/0193867 A1 | 12/2002 | Gladdish et al. | | WO | 95/16406 | 6/1995 |
| 2002/0193868 A1 | 12/2002 | Mitelberg et al. | | WO | 96/24308 | 8/1996 |
| 2002/0193871 A1 | 12/2002 | Beyersdorf et al. | | WO | 96/28115 | 9/1996 |
| 2002/0193872 A1 | 12/2002 | Trout et al. | | WO | 97/07751 | 3/1997 |
| 2002/0193873 A1 | 12/2002 | Brucker et al. | | WO | 97/25938 | 7/1997 |
| 2002/0198584 A1 | 12/2002 | Unsworth et al. | | WO | 97/27820 | 8/1997 |
| 2002/0198587 A1 | 12/2002 | Greenberg et al. | | WO | 97/27959 | 8/1997 |
| 2002/0198588 A1 | 12/2002 | Armstrong et al. | | WO | 97/33533 | 9/1997 |
| 2003/0004559 A1 | 1/2003 | Lentz et al. | | WO | 97/37616 | 10/1997 |
| 2003/0009211 A1 | 1/2003 | DiCarlo | | WO | 97/41804 | 11/1997 |
| 2003/0009212 A1 | 1/2003 | Kerr | | WO | 98/06355 | 2/1998 |
| 2003/0014101 A1 | 1/2003 | Harrison | | WO | 98/10806 | 3/1998 |
| 2003/0045926 A1 | 3/2003 | Pinchasik | | WO | 98/12989 | 4/1998 |
| 2003/0050690 A1 | 3/2003 | Kveen et al. | | WO | 98/27894 | 7/1998 |
| 2003/0055489 A1 | 3/2003 | Kveen et al. | | WO | 98/30156 | 7/1998 |
| 2003/0060871 A1 | 3/2003 | Hill et al. | | WO | 98/33453 | 8/1998 |
| 2003/0074048 A1 | 4/2003 | Sherry | | WO | 98/36708 | 8/1998 |
| 2003/0074050 A1 | 4/2003 | Kerr | | WO | 98/38947 | 9/1998 |
| 2003/0074058 A1 | 4/2003 | Sherry | | WO | 98/41167 | 9/1998 |
| 2003/0083736 A1 | 5/2003 | Brown et al. | | WO | 98/44870 | 10/1998 |
| 2003/0093145 A1 | 5/2003 | Brown et al. | | WO | 98/44873 | 10/1998 |
| 2003/0097170 A1 | 5/2003 | Friedrich et al. | | WO | 98/55047 | 12/1998 |
| 2003/0097174 A1 | 5/2003 | Henderson | | WO | 99/00073 | 1/1999 |
| 2003/0125797 A1* | 7/2003 | Chobotov et al. ......... 623/1.13 | | WO | 99/11199 | 3/1999 |
| 2003/0204244 A1 | 10/2003 | Stiger | | WO | 99/32051 | 7/1999 |
| 2003/0216802 A1 | 11/2003 | Chobotov | | WO | 99/38455 | 8/1999 |
| 2004/0024446 A1 | 2/2004 | Smith | | WO | 99/39662 | 8/1999 |
| 2004/0073190 A1 | 4/2004 | Deem et al. | | WO | 99/39663 | 8/1999 |
| 2004/0073287 A1 | 4/2004 | Golcoechea et al. | | WO | 99/47078 | 9/1999 |
| 2004/0082989 A1 | 4/2004 | Cook et al. | | WO | 99/65419 | 12/1999 |
| 2004/0088044 A1* | 5/2004 | Brown et al. ............... 623/1.16 | | WO | 00/10487 | 3/2000 |
| 2004/0093068 A1 | 5/2004 | Bergen et al. | | WO | 00/33769 | 6/2000 |
| 2004/0098115 A1 | 5/2004 | Goicoechea et al. | | WO | 00/42947 | 7/2000 |
| 2004/0106987 A1 | 6/2004 | Greenberg et al. | | WO | 00/42948 | 7/2000 |
| 2004/0133266 A1 | 7/2004 | Clerc et al. | | WO | 00/45741 | 8/2000 |
| 2004/0210304 A1* | 10/2004 | Seguin et al. ............... 623/2.11 | | WO | 00/51522 | 9/2000 |
| | | | | WO | 00/53251 | 9/2000 |
| FOREIGN PATENT DOCUMENTS | | | | WO | 01/01886 A1 | 1/2001 |
| EP | | 0 480 667 A1 | 4/1992 | WO | 01/01887 A1 | 1/2001 |
| EP | | 0 617 930 A1 | 5/1994 | WO | 01/15633 A1 | 3/2001 |
| EP | | 0 441 516 B1 | 3/1995 | WO | 01/21102 | 3/2001 |
| EP | | 0 646 151 A1 | 4/1995 | WO | 01/21107 | 3/2001 |
| EP | | 0 646 365 A1 | 4/1995 | WO | 01/21108 | 3/2001 |
| EP | | 0 473 694 B1 | 12/1995 | WO | 01/28456 A1 | 4/2001 |
| EP | | 0 689 806 A2 | 1/1996 | WO | 01/30270 A2 | 5/2001 |
| EP | | 0 714 641 A2 | 6/1996 | WO | 01/39700 A1 | 6/2001 |
| EP | | 0 775 472 A3 | 5/1997 | WO | 01/41675 A1 | 6/2001 |
| EP | | 1 029 518 A2 | 8/2000 | WO | 01/52771 A1 | 7/2001 |
| EP | | 1 093 772 A2 | 4/2001 | WO | 01/52914 | 7/2001 |
| EP | | 0 821 648 B1 | 9/2001 | WO | 01/58384 A1 | 8/2001 |
| EP | | 0 808 140 B1 | 12/2001 | WO | 01/66037 A2 | 9/2001 |
| EP | | 1 163 889 A2 | 12/2001 | WO | 01/66038 A2 | 9/2001 |
| EP | | 1 208 817 A2 | 5/2002 | WO | 01/67993 A2 | 9/2001 |
| EP | | 1 212 987 A2 | 6/2002 | WO | 01/74270 A2 | 10/2001 |
| EP | | 1 212 988 A2 | 6/2002 | WO | 02/100454 A1 | 12/2002 |
| | | | | WO | 03/00308 | 1/2003 |

| | | |
|---|---|---|
| WO | 03/003946 A1 | 1/2003 |
| WO | 03/022180 A1 | 3/2003 |
| WO | 03/026713 A1 | 4/2003 |
| WO | 03/094795 A1 | 11/2003 |
| WO | 03/094797 A1 | 11/2003 |
| WO | 03/094799 A1 | 11/2003 |

OTHER PUBLICATIONS

Blum et al., "Abdominal aortic aneurysms: preliminary technical and clinical results with trasfemoral placement of endovascular self-expanding stent-grafts," *Radiology* 198(1):25-31 (1996).

Blum et al., "Endoluminal stent-grafts for infrarenal abdominal aortic aneurysms," *N. Engl. J. Med.*, 336(1):13-20 (1997).

Ernst, "Current therapy for infrarenal aortic aneurysms" *N. Engl. J. Med.*, 336(1):59-60 (1997).

Moore et al., "Transfemoral endovascular repair of abdominal aortic aneurysm: results of the North American EVT phase 1 trial," *J. Vasc. Surg.*, 23(4):543-553 (1996).

Parodi, "Endovascular repair of abdominal aortic aneurysms and other arterial lesions," *J. Vasc. Surg.*, 21(4):549-557 (1995).

Parodi et al., "Transfemoral intraluminal graft implantation for abdominal aortic aneurysms," *Ann. Vasc. Surg.*, 5(6):491-499 (1991).

US 6,413,270, 07/2002, Thornton et al. (withdrawn)

* cited by examiner

RADIALLY EXPANDABLE STENT

ADVANCED ENDOVASCULAR GRAFT

This application is related to U.S. patent application Ser. No. 10/029,570 entitled "Method and Apparatus for Shape Forming Endovascular Graft Material" by Chobotov et al., U.S. patent application Ser. No. 10/029,584 entitled "Endovascular Graft Joint and Method for Manufacture" by Chobotov et al., and U.S. Patent application Ser. No. 10/029,557 entitled "Method and Apparatus for Manufacturing an Endovascular Graft Section", by Chobotov et al. All of the above applications are commonly owned and were filed on even date herewith. All of the above applications are hereby incorporated by reference, each in its entirety.

BACKGROUND

The present invention relates to a system for the treatment of disorders of the vasculature. More specifically, the invention relates to a system for the treatment of disease or injury that potentially compromises the integrity of a flow conduit in the body. For example, an embodiment of the invention is useful in treating indications in the digestive and reproductive systems as well as indications in the cardiovascular system, including thoracic and abdominal aortic aneurysms, arterial dissections (such as those caused by traumatic injury), etc. Such cardiovascular indications often require intervention due to the severity of the sequelae, which frequently is death.

For indications such as abdominal aortic aneurysms, traditional open surgery is still the conventional and most widely-utilized treatment when the aneurysm's size has grown to the point that the risk of aneurysm rupture outweighs the drawbacks of surgery. Surgical repair involves replacement of the section of the vessel where the aneurysm has formed with a graft. An example of a surgical procedure is described by Cooley in Surgical Treatment of Aortic Aneurysms, 1986 (W. B. Saunders Company).

Despite its advantages, however, open surgery is fraught with high morbidity and mortality rates, primarily because of the invasive and complex nature of the procedure. Complications associated with surgery include, for example, the possibility of aneurysm rupture, loss of function related to extended periods of restricted blood flow to the extremities, blood loss, myocardial infarction, congestive heart failure, arrhythmia, and complications associated with the use of general anesthesia and mechanical ventilation systems. In addition, the typical patient in need of aneurysm repair is older and in poor health, facts that significantly increase the likelihood of complications.

Due to the risks and complexities of surgical intervention, various attempts have been made to develop alternative methods for treating such disorders. One such method that has enjoyed some degree of success is the catheter-based delivery of a bifurcated stent-graft via the femoral arteries to exclude the aneurysm from within the aorta.

Endovascular repair of aortic aneurysms represents a promising and attractive alternative to conventional surgical repair techniques. The risk of medical complications is significantly reduced due to the less-invasive nature of the procedure. Recovery times are significantly reduced as well, which concomitantly diminishes the length and expense of hospital stays. For example, open surgery requires an average six-day hospital stay and one or more days in the intensive care unit. In contrast, endovascular repair typically requires a two-to-three day hospital stay. Once out of the hospital, patients benefiting from endovascular repair may fully recover in two weeks while surgical patients require six to eight weeks.

Despite these and other significant advantages, however, endovascular-based systems have a number of shortcomings. Present bifurcated stent-grafts require relatively large delivery catheters, often up to 24 French and greater in diameter. These catheters also tend to have a high bending stiffness. Such limitations result in the need for a surgical cut-down to deliver the stent-graft and make delivery through the often narrow and irregular arteries of diseased vessels difficult and risky. Because of this, endovascular treatment of aortic aneurysmal disease is not available to many patients who could otherwise benefit from it. For instance, women statistically tend to have smaller vessels and therefore some are excluded from many current endovascular therapies simply due to this reason. There is therefore a need for an endovascular stent-graft capable of being delivered via a smaller and more flexible delivery catheter. Even greater advantages may be realized if such an endovascular stentgraft is capable of being delivered percutaneously.

Further, an endovascular stent-graft must withstand tremendous pulsatile forces over a substantial period of time while remaining both seated and sealed within the vessel. In order to achieve these objectives, the device, which may comprise component parts and/or materials, must remain intact. The device must resist axial migration from the site of deployment while being subjected to significant pulsatile forces, and it should have sufficient radial compliance to conform to the vessel anatomy within which it is deployed so as to prevent blood leakage between the device and the vessel wall at both its proximal, or cephalic, end as well as at its distal, or caudal end or ends (where the net force may be retrograde). Such a device should conform to the morphology of the treated vessel, without kinking or twisting, over the life of the patient.

SUMMARY

The present invention generally is directed to a system for the endovascular treatment of body passageways that includes a medical device implantable within a body lumen such as a blood vessel. Some embodiments of this invention include an endovascular graft for treating vascular disease.

One embodiment includes a graft with a graft body section having a proximal end and a distal end, and, disposed or affixed on at least one end, a connector member having one or more connector member connector elements. The connector member may be embedded within multiple layers of the graft body section. A stent may be coupled or affixed to the one or more connector member connector elements via one or more stent connector elements. The graft may include a proximal stent and connector member only, a distal stent and connector member only, or both proximal and distal stents and their respective connector members.

Both the connector member connector elements and the stent connector elements may have a proximal end and a distal end that comprise opposing shoulder portions. The graft may further have one or more coupling members, such as a wire coil, configured to couple or connect the one or more connector member connector elements to the one or more stent connector elements.

Both the connector members and the stents may be formed of a serpentine ring having one or more apices. One embodiment includes a graft having single stage distal and/or proximal stents in which the associated connector member may have twice as many apices as the stent. In another embodiment, the graft has two-stage distal and/or proximal stents with twice as many apices in a first region as in a second region while the associated connector member has the twice the number of apices as in the first region of the stent. For example, a useful embodiment is one in which a twelve-apex connector member is connected to a first six-apex or six-crown region of a proximal or distal stent and that stent has a second three-apex or three-crown region integral with or joined to the six-crown region.

In alternative embodiments, grafts that include various combinations of single and multiple-stage proximal and distal stents with their associated connector members are possible.

The stents may also include one or more barbs. Typically, the barbs on a proximal stent are oriented distally to engage the stent into the tissue wall in the proximal-to-distal flow field in which the graft is typically disposed. Likewise, in applications in which the graft is deployed to treat an abdominal or thoracic aortic aneurysm, the barbs on one or more distal stents are typically oriented proximally to engage the stent into the tissue wall to oppose the typically retrograde migration forces. The barbs may range in length from about 1 to about 5 mm. They will typically project radially outward from a longitudinal axis of their respective stent and form a barb radial angle from about 10 to about 45 degrees with respect to the graft proximal neck portion inlet axis when the stent is deployed in vivo. The barbs may also be laterally biased in a plane that is orthogonal to a plane in which the barb radial angle is formed to form a barb kick angle.

The stent or stents (proximal and/or distal) comprise struts having one or more optional barb tuck pads integral to the struts such that when the proximal stent is in a reduced profile delivery configuration, each barb is retained by the stent strut. When the endovascular graft is in a deployed configuration, the one or more barbs are released.

The stent or stents may also comprise optional barb tuck slots configured to receive the barbs such that each barb is retained by a slot when the stent is in a delivery configuration. In a deployed configuration, the barbs are released from their corresponding barb tuck slots.

In addition, the stent may comprise grooves. In a typical delivery system, some type of belts or sutures may be used to help retain the endovascular graft in its compressed delivery configuration. The grooves may accommodate these belts or sutures without increasing the small diameter delivery of the device.

The graft body section may also have one or more inflatable cuffs disposed on or near the graft body section proximal end, distal end, or both. The inflatable cuffs provide a sufficiently stiff structure when inflated which help to support the graft body section and provide a conformable surface to seal the graft against the interior surface of the vessel in which it is deployed.

The graft body section may also include one or more inflatable channels. The channel or channels typically may be disposed between and in fluid communication with either or both proximal and distal inflatable cuffs. The channel or channels enhance the graft body section stiffness upon their inflation, help to prevent kinking of the graft body section, and may also facilitate deployment of the graft within a patient's body passageway. The inflatable channel or channels can be in a longitudinal and/or linear configuration with respect to the graft body section, but alternatively may take on a helical or circumferential configuration. Other orientations such as interconnecting grids or rings may also be suitable alone or in combination with any of the other configurations.

During deployment of the graft, the inflatable cuff or cuffs and channel or channels may be inflated or injected with a material that may comprise one or more of a solid, fluid (gas and/or liquid), gel or other medium. According to the invention, a useful inflation medium includes the combination polyethylene glycol diacrylate, pentaerthyritol tetra 3(mercaptopropionate) and a buffer such as glycylglycine or triethanolamine in phosphate-buffered saline. Saline or another inert biocompatible liquid may be added to this three-component inflation medium in amounts up to about sixty percent of the total inflation medium volume. Radiopaque materials such as tantalum, iodinated contrast agents, barium sulfate, etc. may be added to this three-component medium, typically in the buffer, so to render the inflation medium visible under fluoroscopy.

In another embodiment of the invention, the graft may comprise a main body portion and a first bifurcated portion forming a continuous lumen that is configured to confine a flow of fluid therethrough. The graft may also include a second bifurcated portion in fluid communication with the main body portion. At least one inflatable cuff may be disposed at either or both a proximal end of the main body portion and a distal end of the first bifurcated portion. One or more inflatable channels may be disposed between the inflatable cuffs as previously described, and may extend over some or all of the main body portion. The cuffs and channels may be filled with an inflation medium, optionally diluted with an inert biocompatible material such as saline or other liquid, as described above.

In yet another embodiment of the invention, the graft may comprise a main body portion in fluid communication with a first and a second bifurcated portion forming a continuous bifurcated lumen, said lumen configured to confine a flow of fluid therethrough. At least one inflatable cuff may be disposed at or near either or both a proximal end of the main body portion and a distal end of the first and second bifurcated portions. One or more inflatable channels may be disposed between the inflatable cuffs as previously described, and may extend over some or all of the main body portion.

The proximal ends of the graft main body portion may have connector members comprising one or more connector elements, and a proximal stent coupled to the one or more connector elements. One or both of the first and/or second bifurcated portions may likewise have first and/or second distal connector members comprising one or more connector elements disposed on their respective distal ends, and a distal stent coupled to the first and/or second distal connector members.

The present invention is also a system for implanting a tubular medical device within a body lumen having a wall, including a stent for affixing the medical device to the body lumen wall and a connector member for coupling the stent to the medical device, wherein the stent and the connector member are coupled to one another by at least one set of connector elements.

One or more barbs may also be included in this system. In addition, one or more barb tuck pads may be included in which the one or more barbs are configured to be retained by the one or more barb tuck pads when the system is in a delivery configuration and released by the one or more barb tuck pads when the system moves to a deployed configuration. The stent may further include optional slots configured to receive the barbs when the system is in a delivery configuration and wherein the barbs are configured to be released from the slots when the system is in a deployed configuration.

The invention also includes an endovascular graft comprising a graft body section with a proximal end and a distal end and a proximal connector member affixed to the proximal end of the graft body section. The proximal connector member may have one or more connector elements.

The graft may also have a proximal stent comprising one or more distally oriented barbs and one or more proximal stent connector elements coupled to the one or more proximal connector member connector elements and a distal connector member affixed to the distal end of the graft body section. The distal connector member may include one or more connector elements.

The graft of this embodiment further includes a distal stent comprising one or more proximally oriented barbs and comprising one or more distal stent connector elements coupled to the one or more distal connector member connector elements, one or more inflatable cuffs disposed at or near each of the proximal and distal ends of the graft body section, and wherein the graft body section comprises an inflatable channel in fluid communication with the proximal and distal cuffs.

In addition, the proximal and distal connector member connector elements may each have opposing shoulder portions on their proximal and distal ends, as may the proximal and distal stent connector elements. One or more coupling members may couple the proximal connector member connector elements to the proximal stent connector elements and likewise couple the one or more distal connector member connector elements to the one or more distal stent connector elements.

At least one of the inflatable channel, the distal inflatable cuff, and the proximal inflatable cuff may contain an inflation medium comprising the combination polyethylene glycol diacrylate, pentaerthyritol tetra 3(mercaptopropionate), and a buffer.

The proximal stent barbs or distal stent barbs of this embodiment may have a length from about 1 to about 5 mm, and the graft body section may comprise ePTFE.

In yet still a further bifurcated embodiment of the present invention, the device includes a main body portion with a distal end and a proximal end with a connector member disposed on the proximal end. The connector member may include one or more connector elements.

The proximal stent of this embodiment may comprise one or more distally oriented barbs and one or more proximal stent connector elements that are coupled to the connector member connector elements.

This embodiment further includes a first bifurcated portion and a second bifurcated portion forming a continuous lumen with the main body portion. This lumen is configured to confine a flow of fluid therethrough.

A distal connector member may be disposed on distal ends of each of the first and second bifurcated portions. Each of these distal connector members includes one or more connector elements. In addition, this embodiment has one or more distal stents with at least one proximally oriented barb and comprising one or more distal stent connector elements. The distal stent connector elements are coupled to the distal connector member connector elements on one or both of the first and second bifurcated portions.

This embodiment also includes at least one inflatable channel extending from one or both of the first and second bifurcated portions to the main body portion, at least one inflatable cuff disposed at or near a proximal end of the main body portion in fluid communication with the at least one channel, and an inflatable cuff disposed at or near a distal end of each of the first and second bifurcated portions.

The proximal and distal connector member connector elements may each have opposing shoulder portions on their proximal and distal ends, as may the proximal and distal stent connector elements. One or more coupling members may couple the proximal connector member connector elements to the proximal stent connector elements and likewise couple the one or more distal connector member connector elements to the one or more distal stent connector elements.

At least one of the inflatable channel, the first bifurcated portion distal inflatable cuff, the second bifurcated portion distal inflatable cuff, and the proximal inflatable cuff may contain an inflation medium comprising the combination polyethylene glycol diacrylate, pentaerthyritol tetra 3(mercaptopropionate), and a buffer.

The proximal and/or distal stent barbs may have a length from about 1 to about 5 mm. The graft main body portion as well as the first and second bifurcated portions may comprise ePTFE.

These and other advantages of the invention will become more apparent from the following detailed description of the invention when taken in conjunction with the accompanying exemplary drawings.

DETAILED DESCRIPTION

Figure 1:
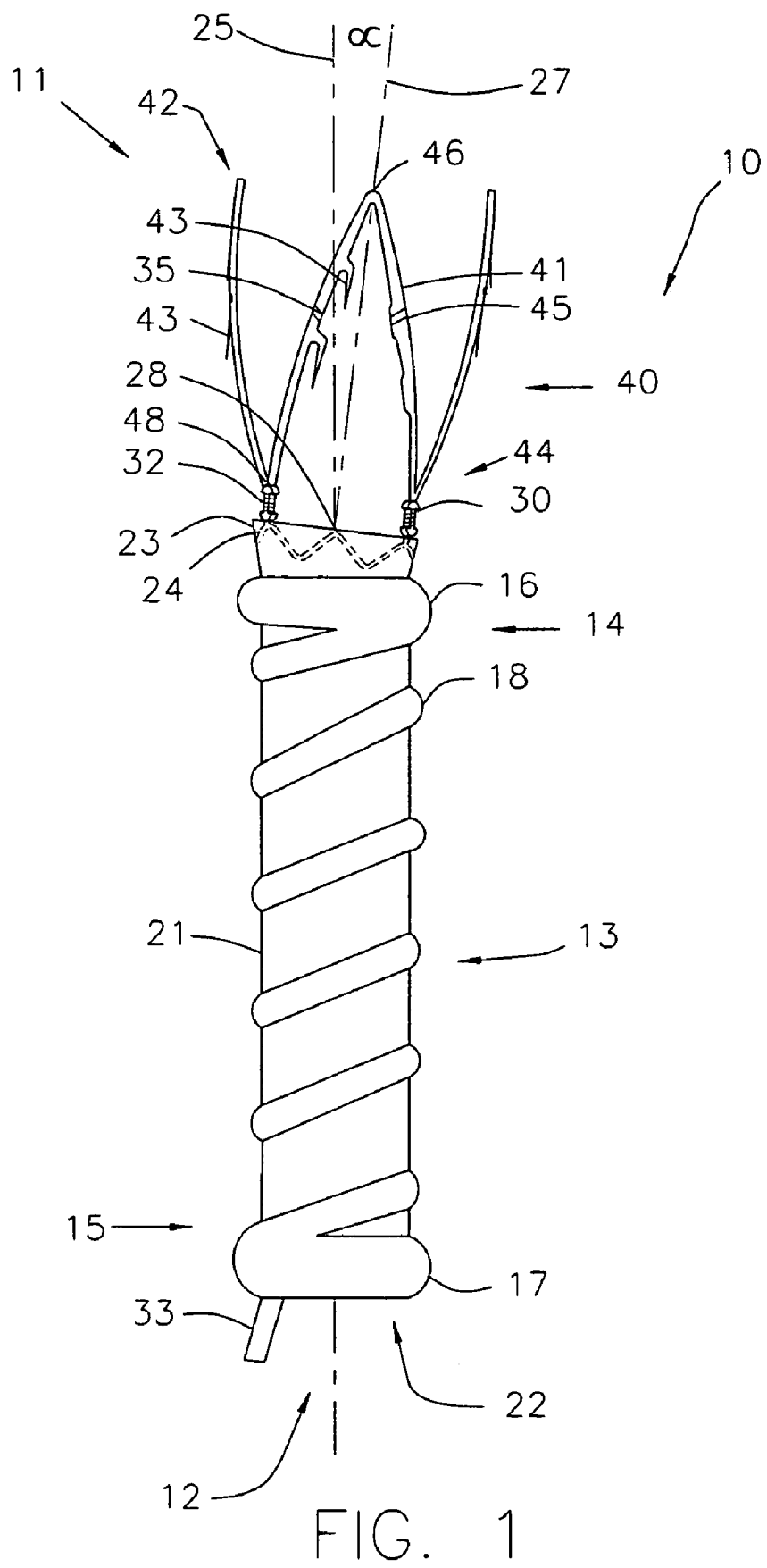
FIG. 1 shows an endovascular graft according to an embodiment of the present invention.

FIG. 1 shows an endovascular graft 10 in its deployed configuration. Unless otherwise stated, the term "graft" or "endovascular graft" is used herein to refer to a prosthesis capable of repairing and/or replacing diseased vessels or portions thereof, including generally tubular and bifurcated devices and any components attached or integral thereto. For purposes of illustration, the graft embodiments described below are assumed to be most useful in the endovascular treatment of abdominal aortic aneurysms (AAA). For the purposes of this application, with reference to endovascular graft devices, the term "proximal" describes the end of the graft that will be oriented towards the oncoming flow of bodily fluid, typically shows a flat pattern blood, when the device is deployed within a body passageway. The term "distal" therefore describes the graft end opposite the proximal end. Finally, while the drawings in the various figures are accurate representations of the various embodiments of the present invention, the proportions of the various components thereof are not necessarily shown to exact scale within and among or between any given figure(s).

Graft 10 has a proximal end 11 and a distal end 12 and includes a generally tubular structure or graft body section 13 comprised of one or more layers of fusible material, such as expanded polytetrafluoroethylene (ePTFE). A proximal inflatable cuff 16 is disposed at or near a proximal end 14 of graft body section 13 and an optional distal inflatable cuff 17 is disposed at or near a graft body section distal end 15. Graft body section 13 forms a longitudinal lumen 22 configured to confine a flow of fluid therethrough and may range in length from about 5 to about 30 cm; specifically from about 10 to about 20 cm.

As will be described in greater detail below, inflation of cuffs 16 and 17 will cause them to assume a generally annular shape (especially when graft body section 13 is in an unconstrained state). Inflatable cuffs 16 and 17 will generally, however, conform to the shape of the vessel within which it is deployed. When fully inflated, cuffs 16 and 17 may have an outside diameter ranging from about 10 to about 45 mm; specifically from about 16 to about 32 mm.

At least one inflatable channel 18 may be disposed between and in fluid communication with proximal inflatable cuff 16 and distal inflatable cuff 17. Inflatable channel 18 provides structural support to graft body section 13 when inflated to contain an inflation medium. Inflatable channel 18 further prevents kinking and twisting of the tubular structure or graft body section when it is deployed within angled or tortuous anatomies as well as during remodeling of body passageways (such as the aorta and iliac arteries) within which graft 10 is deployed. Together with proximal and distal cuffs 16 and 17, inflatable channel 18 forms a network of inflatable cuffs and channels in fluid communication with one other.

We have found the helical configuration of channel 18 in the FIG. 1 embodiment to be particularly effective in providing the needed kink resistance for effectively treating diseased body passageways such as AAAs, in which highly angled and tortuous anatomies are frequently found. In alternative embodiments, however, other cuff and channel configurations are possible. Inflatable channel 18 may be disposed helically as shown in FIG. 1, it may take on a more circumferential or annular rib and spine configuration as shown in the FIG. 2 embodiment, or otherwise. Similarly, the longitudinal and radial dimensions of inflatable channel 18 may vary as necessary both between different graft body sections and even within a single graft body section, depending on the indication for which graft 10 is intended to treat. Further, inflatable channel 18 may be oriented at various angles with respect to the longitudinal axis 25 of graft body section 13, and the pitch (the distance between helical or parallel windings of channel 18) may vary as necessary.

In the embodiment of FIG. 1, the channel pitch, or distance between each helical inflatable channel 18 winding, may range from about 2 to about 20 mm, depending on the overall size of graft body section 13 and the desired degree of kink resistance. We have found that a pitch of between about 4 and about 10 mm is effective for tubular embodiments of the present invention and a pitch of between about 3 and about 10 mm to be useful in bifurcated graft embodiments. The helix angle of each channel winding (measured with respect to a plane perpendicular to the graft body section longitudinal axis 25) may range from about 10 to about 45 degrees; more specifically, from about 20 to about 35 degrees in tubular and bifurcated graft embodiments. Finally, the width of inflatable channel 18 typically ranges from about 1 to about 8 mm; more specifically, from about 2 to about 4 mm. Graft body section or tubular structure 13 and its associated components may be made from a variety of suitable materials, including ultra high molecular weight polyethylene, polyesters, and the like. As previously discussed, we have found constructing graft body section 13 primarily from one or more layers of ePTFE to be particularly useful. Details of how graft 10 may be fabricated (as well as all of the other grafts discussed herein) are more fully described in copending U.S. patent application Ser. Nos. 10/029,570, 10/029,584, and 10/029,557 each to Chobotov et al. In addition, U.S. patent application Ser. No. 09/133,978 to Chobotov, filed Feb. 9, 1998 and entitled "Endovascular Graft" (now U.S. Pat. 6,395,019) and copending U.S. patent application Ser. No. 09/917,371 to Chobotov et al., filed Jul. 27, 2001 and entitled "Bifurcated Stent-Graft Delivery System and Method", (now U.S. Pat. 6,132,457) the entirety of each of which are hereby incorporated herein by reference, teach a useful endovascular stent-graft and delivery system, respectively.

A proximal neck portion 23 is disposed in the vicinity of graft body section proximal end 14 and serves as an additional means to help seal the deployed graft against the inside of a body passageway. Proximal neck portion 23 has an inlet axis 27 that forms an inlet axis angle a in relation to graft body section longitudinal axis 25. This angled inlet axis 27 allows the graft to better conform to the morphology of a patient's vasculature in patients who have an angled vessel morphology, such as is often the case in the neck region of abdominal aortic aneurysms. The inlet axis angle a may range in any direction with respect to longitudinal axis 25 from about zero to about 90 degrees, preferably from about 20 to about 30 degrees. Proximal neck portion 23 may be tapered or flared to a larger diameter in the proximal direction to facilitate this sealing function. Proximal neck portion 23 also serves as a means of providing a smooth fluid flow transition into graft lumen 22.

The network of inflatable cuffs 16, 17 and channel 18 may be inflated, most usefully in vivo, by introduction or injection of a material or medium through an injection port 33 that is in fluid communication with cuff 17 and the associated cuff/channel network. The material may comprise one or more of a solid, fluid (gas and/or liquid), gel or other medium. The material may contain a contrast medium that facilitates imaging the device while it is being deployed within a patient's body. For example, radiopaque materials containing elements such as bismuth, barium, gold, iodine, platinum, tantalum or the like may be used in particulate, liquid, powder or other suitable form as part of the inflation medium. Liquid iodinated contrast agents are a particularly suitable material to facilitate such imaging. Radiopaque markers may also be disposed on or integrally formed into or on any portion of graft 10 for the same purpose, and may be made from any combination of biocompatible radiopaque materials.

A connector member 24 is affixed to or integrally formed in graft body section 13, or as shown in FIG. 1, at or near graft body section proximal end 14 and proximal neck portion 23. Connector member 24 is a serpentine ring structure comprising apices 28. Connector member 24 may be made from any suitable material that permits expansion from a constrained state, most usefully a shape memory alloy having superelastic properties such as nickel titanium (NiTi). Other suitable connector member 24 materials include stainless steel, nickel-cobalt alloys such as MP35N, tantalum and its alloys, polymeric materials, composites, and the like. Connector member 24 (as well as all stents and connector members described herein) may be configured to self-expand from a radially constrained state or be configured to expand as a result of an applied force (such as from an inflated balloon), or, in the case of some shape memory materials, a temperature change.

The configuration of connector member 24 shown in FIG. 1 comprises eight apices 28 (put more precisely, the FIG. 1 connector member 24 comprises eight proximal apices and eight distal apices; however, unless otherwise mentioned, the term "apices" refers in this context to either the proximal or distal set of apices in a single connector member, stent, or stent portion). Another particularly useful configuration is one shown in FIGS. 2–7 in which the connector member comprises twelve apices. Any number of apices up to twenty-four or more may be used in connector member 24. In general terms, as the number of apices 28 on connector member 24 increase, connector member 24 will exhibit a greater conformability to the vessel wall when it is expanded from a radially constrained state.

No matter the number of apices present, one function of connector member 24 is to work in conjunction with proximal neck 23 in which it is typically embedded to help seal the deployed graft against the inside of a body passageway as previously described. It can also play a role in helping to keep graft 10 in place within the vessel wall and may also facilitate the opening of graft body section proximal end 14 during deployment.

Some apices 28 may also comprise a connector member connector element 30, described more fully below with respect to the embodiment of FIG. 2. In the FIG. 1 embodiment, in which connector member 24 comprises eight (proximal) apices 28, a connector element 30 is distributed on every other apex 28. We have found this configuration to be suitable for meeting the various performance requirements of the present invention. Other configurations are possible, including the twelve-apex connector member 24 shown in FIGS. 2–7 comprising six connector elements 30 distributed on every other apex 28. Other configurations in which, for example, connector elements are distributed on every apex, every third or fourth apex, or any other pattern are within the scope of the present invention.

Graft 10 further comprises a proximal stent 40 having a proximal end 42 and a distal end 44. Although other configurations are possible, proximal stent 40 in the FIG. 1 embodiment comprises a serpentine ring having four apices 46, or half the number of apices 28 of connector member 24. Note that proximal stent 40 in FIG. 1 takes on an optional tulip-shaped tapered profile in which the stent's diameter varies along its length. Such a profile serves to present sufficient radial force upon radial expansion of stent 40 to reliably anchor graft 10 to the vessel or lumen wall within which it is deployed while, at its tapered distal end near graft body section 13, refraining from interfering with the sealing function performed by proximal cuff 16, proximal neck portion 23, and connector member 24. This profile also accommodates any taper that may be present in the host vessel or lumen.

As shown in FIG. 1, proximal stent 40 is disposed generally proximal to graft body section 13 and connector member 24. Proximal stent is typically, though not necessarily, made a part of graft 10 by being affixed or connected to connector member 24 via connector elements as described in detail below. Proximal stent 40 may also be affixed or embedded directly to or in proximal neck portion 23 and/or other portions of graft body section 13. In addition, the present invention includes embodiments wherein the connector member and proximal stent are not mechanically or otherwise fastened to one another but rather unified, formed of a monolithic piece of material such as NiTi.

This configuration of proximal stent 40, connector member 24, proximal neck portion 23, and proximal cuff 16 helps to separate the sealing function of proximal cuff 16, which requires conformation and apposition to the vessel wall within which graft 10 is deployed without excessive radial force, from the anchoring function of proximal stent 40 (connector member 24 and proximal neck portion 23 play intermediate roles). This allows the sealing and anchoring functions each to be optimized without compromising the other. In addition, in part because proximal stent 40, connector member 24, and inflatable cuff 16 are longitudinally distributed along the graft body section longitudinal axis 25, a smaller, more flexible delivery profile ranging from about 10 to about 16 French is possible; preferably below 12 French.

Proximal stent 40 may be manufactured from any of the materials suitable for connector member 24. When manufactured from a shape memory alloy having superelastic properties such as NiTi, proximal stent 40 may be configured to self-expand upon release from a constrained state.

Proximal stent 40 further comprises proximal stent connector elements 48 that are affixed to connector member connector elements 30 via coupling members as described more fully below in relation to FIGS. 2-6. Note that in the FIG. 1 embodiment, there is one proximal stent connector element 48 for every connector member connector element 30.

Proximal stent 40 also comprises struts 41 and may also comprise one or more barbs 43. A barb can be any outwardly directed protuberance, typically terminating in a sharp point that is capable of at least partially penetrating a body passageway in which graft 10 is deployed (typically the intimal and medial layers of a blood vessel such as the abdominal aorta).

When proximal stent 40 is deployed in the abdominal aorta, for example, typically in a location proximal to the aneurysm and any diseased tissue, barbs 43 are designed to work in conjunction with the distally-oriented blood flow field in this location to penetrate tissue and prevent axial migration of graft 10. This is why barbs 43 in the FIG. 1 embodiment are oriented distally with respect to graft body section 13.

In alternative embodiments, depending upon the material used in the manufacture of proximal stent 40, the clinical demands and other factors, the degree to which barbs 43 help maintain the position of graft 10 within the vessel may vary. Consequently, the number, dimensions, configuration and orientation of barbs 43 may vary significantly, yet be within the scope of the present invention.

Figure 1A:
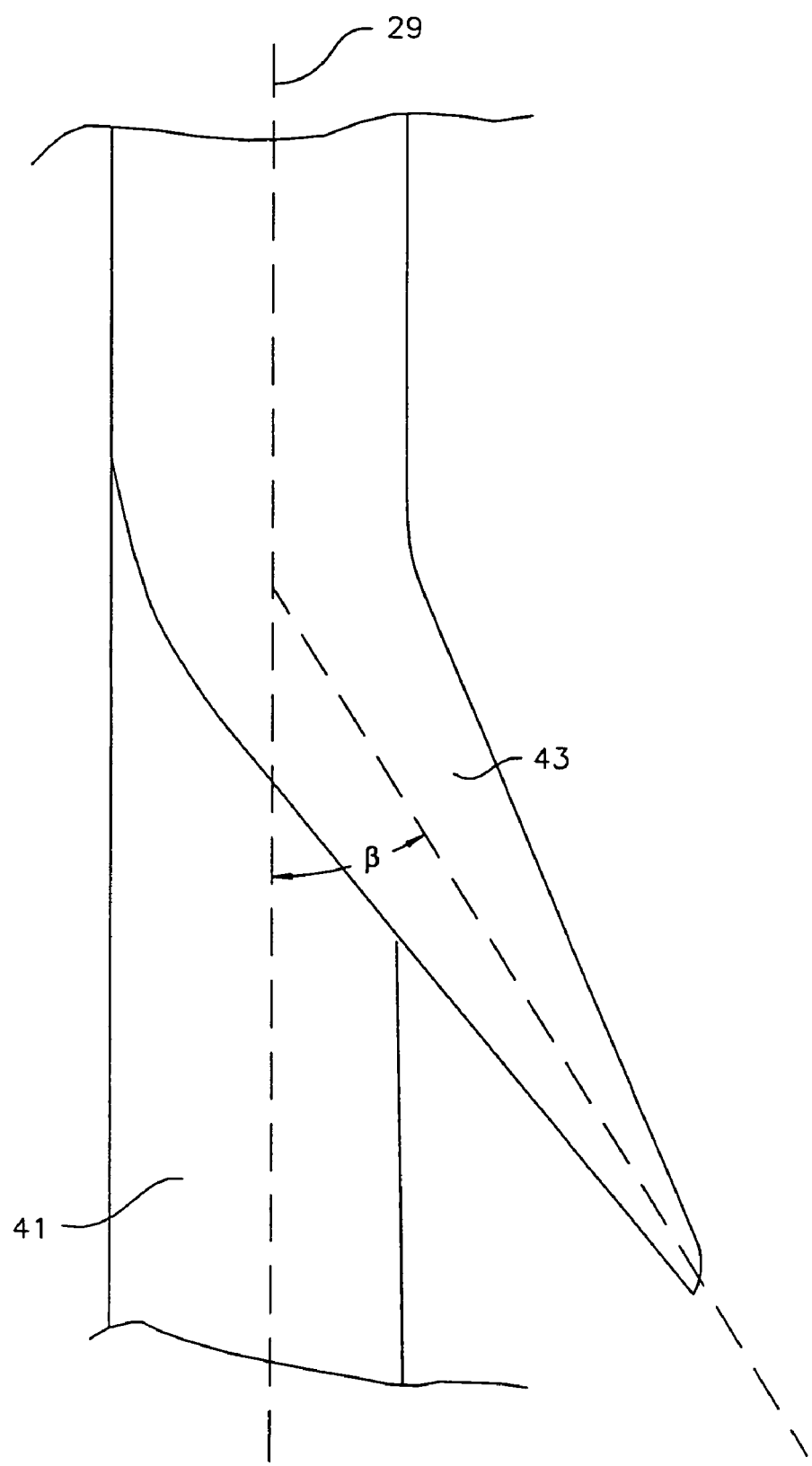
FIGS. 1A–1B detail two angles at which a stent barb may be oriented on the graft of an embodiment of the present invention.
Figure 1B:
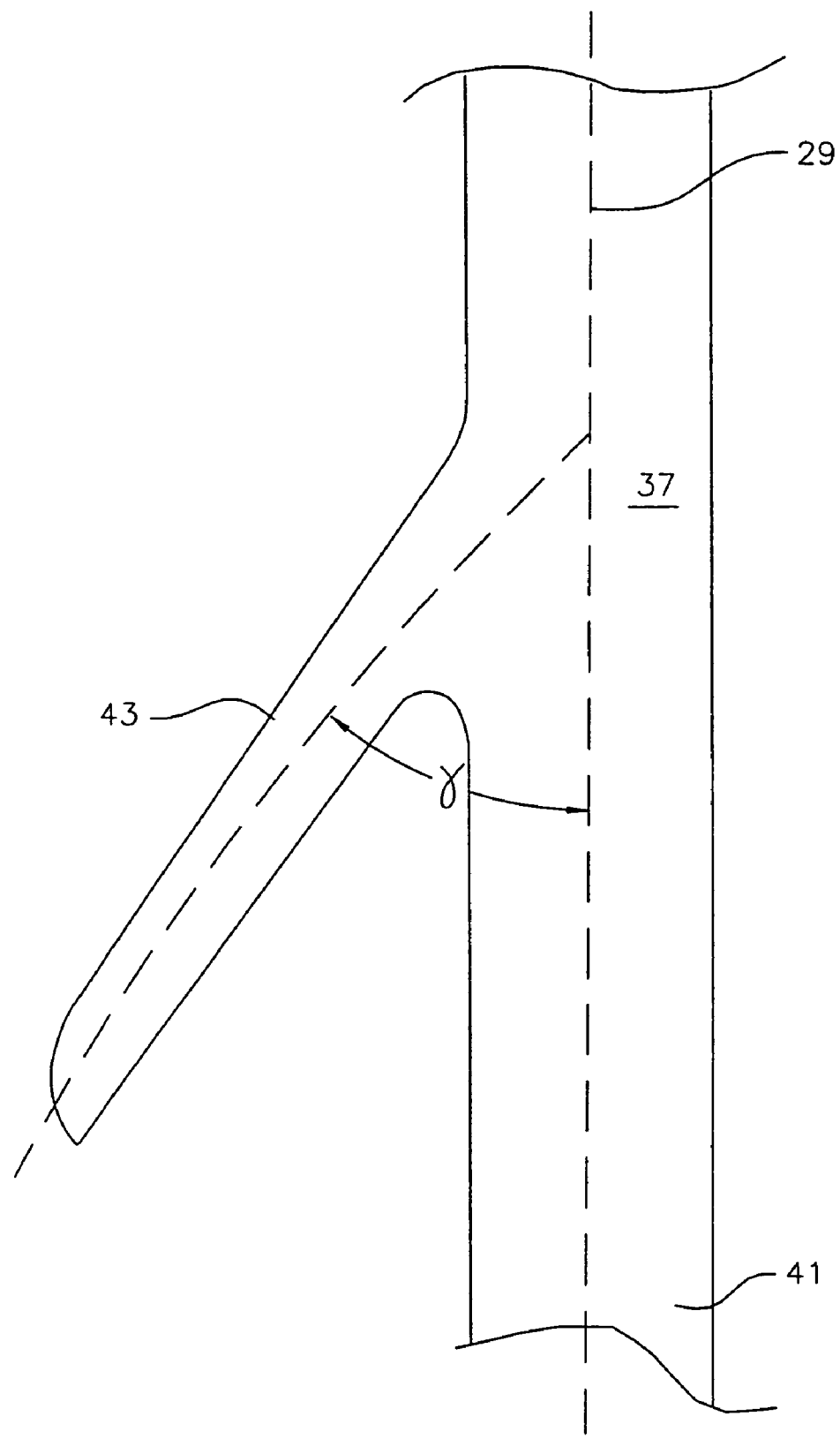

The length of barbs 43 in any of the embodiments of the present invention may range from about 1 to about 5 mm; more particularly, from about 2 to about 4 mm. As shown in their free expanded configuration in FIG. 1 and as shown in greater detail in FIG. 1A, barbs 43 may be oriented in a distal direction and form an elevation angle β ranging from about 10 to about 45 degrees or higher with respect to a longitudinal axis 29 of strut 41, projecting generally radially outward from graft lumen 22 away from proximal neck inlet axis 27. Disposing barbs at angle βprovides the necessary embedding force to anchor graft 10 into the vessel or lumen in which it is deployed. Although not shown in the figures, the barb elevation may also be described when the graft 10 is deployed in vivo in a body lumen or vessel by a second angleβ' measured relative to proximal neck inlet axis 27. This second barb elevation angle β' will typically range from about 5 to about 45 degrees. For both barb elevation anglesβ' and β', similar orientations may be found with barbs in other embodiments of the present invention. It is generally desirable that barbs 43 be oriented in a position generally parallel to the axis of the lumen in which they are deployed so that they are in a position to best resist the drag loads imposed by the flow field in vivo in certain applications. To this end, we have found it useful for one or more of barbs 43 to form an optional second barb azimuth or "kick" angle γ with respect to strut longitudinal axis 29 as shown in FIG. 1B. In this view, barb 43 is laterally biased in a plane that is tangent to an outside surface 37 of strut 41 and generally orthogonal to a plane in which angle γ is formed. The term "strut outside surface 37" generally refers to that portion of the surface of strut 41 located opposite the proximal neck inlet axis 27, or that portion of strut 41 that when deployed will be in direct contact with the vessel or lumen wall. We have also found that providing lateral kick angle γ to barbs 43 contributes to greater barb stability when the barb is tucked behind an adjacent strut or tuck pad in a reduced diameter delivery configuration. In proximal stent 40, γ may range from between about 5 and about 70 degrees relative to strut axis 41. Similar orientations may be found with barbs in other embodiments of the present invention.

The number of barbs, the length of each barb, each of the barb angles described above, and the barb orientation may vary from barb to barb within a single stent or between multiple stents within a single graft.

Note that although the various barbs (and tuck pads 45 discussed below) discussed herein may be attached to or fixed on the stent struts 41, we have found it useful that, as shown in the various figures, they be integrally formed as part of the stent struts. In other words, they can be mere extensions of the struts in which no joint or other connection exists. Because there is no joint, we have found the strength of the barb/strut interface to be very high, as is the fatigue resistance of the barbs. With no mechanical connection to join the barbs to the struts, reliability of the barb/strut interface is higher. In addition, the lack of a heat-affected zone in which the mechanical properties of a welded or brazed joint may be deleteriously affected is another significant advantage to having the barbs and tuck pads be integral to the stent.

Struts 41 may also comprise optional integral tuck pads 45 disposed opposite each barb 43. As is the case with the barbs, the number, dimensions, configuration and orientation of barb tuck pads 45 may vary significantly.

During preparation of graft 10 (and therefore proximal stent 40) into its reduced diameter delivery configuration, each barb 43 is placed behind a corresponding strut 41 (and optional tuck pad 45, if present) so to thereby prevent that barb from contacting the inside of a delivery sheath or catheter during delivery of the device and from undesired contact with the inside of a vessel wall. As described in copending U.S. patent application Ser. No. 09/917,371 to Chobotov et al., a release belt disposed in one or more grooves 35 disposed on struts 41 retain proximal stent 40 in this delivery configuration.

Upon deployment of graft 10, and more particularly, proximal stent 40, (typically accomplished in part by release of this and other belts), the radial expansion of stent 40 results in a displacement of struts 41 so that the distance between them increases. Eventually this displacement becomes large enough so to free the barbs from behind the adjacent strut (and optional tuck pad 45, if present) and engage the wall of the lumen being treated. During experiments in which stents of the present invention having barbs described herein are released from a constrained delivery configuration to assume an expanded or deployed configuration, high speed video confirms that the barbs tend to release with a time constant that is generally an order of magnitude lower than the time constant associated with the radial expansion of the stent. In other words, during the stent deployment process, their barbs complete their deployment before the stent is fully expanded, so that the barbs may engage the vessel or lumen wall with maximum effectiveness.

Alternatively, and especially in the case when a different material such as stainless steel is used for proximal stent 40, an optional balloon may be used to expand stent 40 to free barbs 43 from their tuck pads 45 and to cause barbs 43 to engage tissue as desired. Even if a superelastic self-expanding proximal stent 40 is used in graft 10, such a balloon may be used to help further implant barbs 43 into their desired position to ensure proper placement of graft 10.

Figure 2:
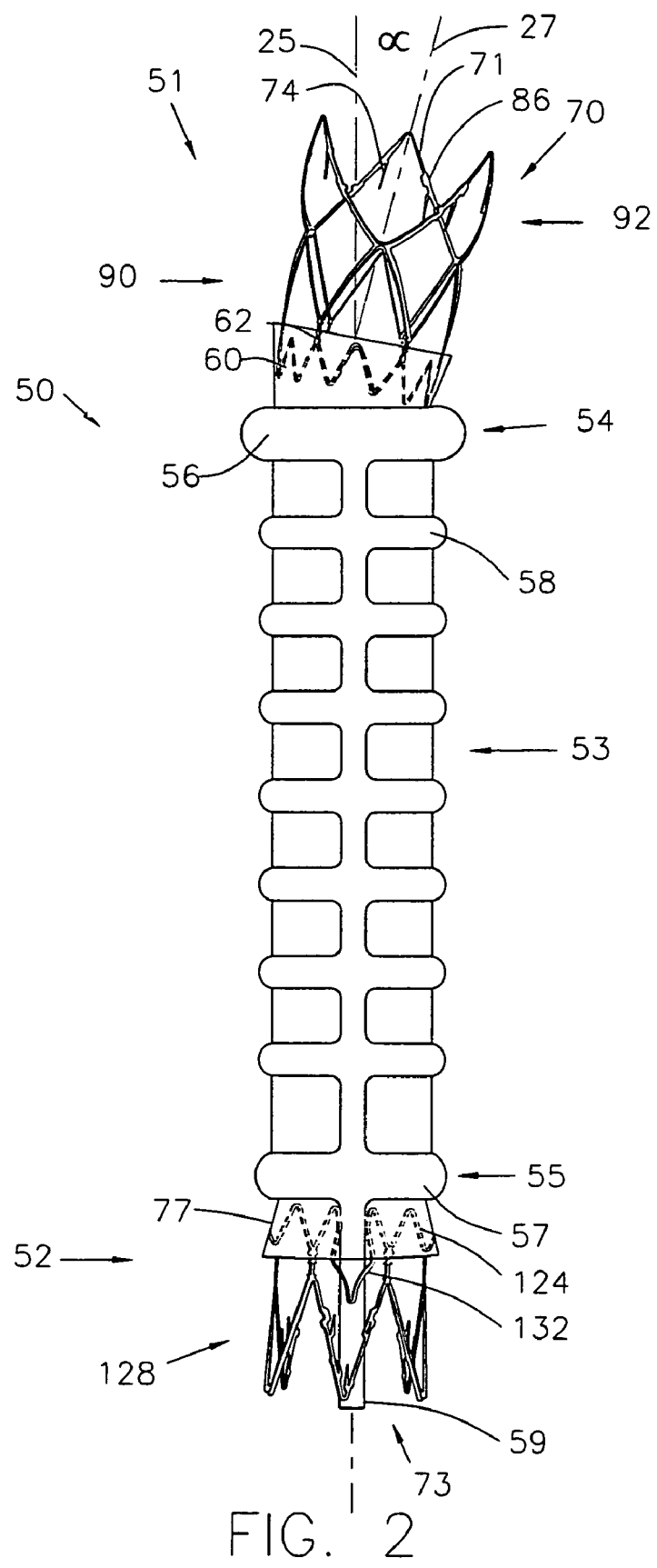
FIG. 2 shows a second endovascular graft according to an embodiment of the present invention.

Turning now to FIG. 2, another endovascular graft having features of the present invention is illustrated. Graft 50 has a proximal end 51 and a distal end 52 and comprises a tubular structure or graft body section 53 with a proximal end 54 and distal end 55. As with the FIG. 1 embodiment, graft body section 53 forms a longitudinal lumen 73 configured to confine a flow of fluid therethrough and may range in length from about 5 to about 30 cm; specifically from about 10 to about 20 cm. Proximal inflatable cuff 56 and optional distal inflatable cuff 57 form a seal when inflated to help prevent transmission of pressure (hemodynamic pressure when the fluid is blood) to the lumen or vessel walls in the region between the proximal and distal cuffs. In addition, the cuffs help to prevent flow of fluid such as blood around the outer surface of graft body section 53.

Inflatable channel 58 comprises an inflatable longitudinal channel or spine in fluid communication with a series of approximately parallel inflatable circumferential channels or ribs. We have found this configuration to be particularly useful in providing effective kink resistance while allowing for rapid and relatively easy inflation of the cuffs and channels when using more viscous inflation materials. Channel 58 is in fluid communication with proximal and distal cuffs 56 and 57, forming a network of inflatable cuffs and channels in fluid communication with each other. Fill port 59 is in fluid communication with distal cuff 57, inflatable channel 58, and proximal cuff 56, adding to this network for the introduction of an inflation medium into graft body section 53. Features of the FIG. 1 embodiment not discussed herein may be present in the FIG. 2 device.

Graft 50 of FIG. 2 also comprises a twelve-crown or twelve-apex proximal connector member 60, a two-stage six- and three-crown proximal stent 70, distal neck portion 77, distal connector member 124, and distal stent 128. Distal connector member 124 and distal stent 128 are analogous to connector member 60 and proximal stent 70 except that the distal stent in the FIG. 2 embodiment is single-stage and its optional barbs face in the opposite, or proximal direction relative to the barbs 74 of proximal stent 70. Distal connector member 124 is affixed or attached to distal stent 128, both of which are more fully described in relation to a bifurcated version of the present invention shown in FIGS. 8 and 9, respectively. Distal connector member 124 and distal stent 128 may be manufactured from materials and according to methods that are suitable for connector member 60 and proximal stent 70. Further, distal connector member 124 may be attached to, affixed to, formed integrally with tubular structure or graft body section 53, or more typically, distal neck portion 77. Distal connector member 124 further comprises fill port bridge 132.

Figure 3:
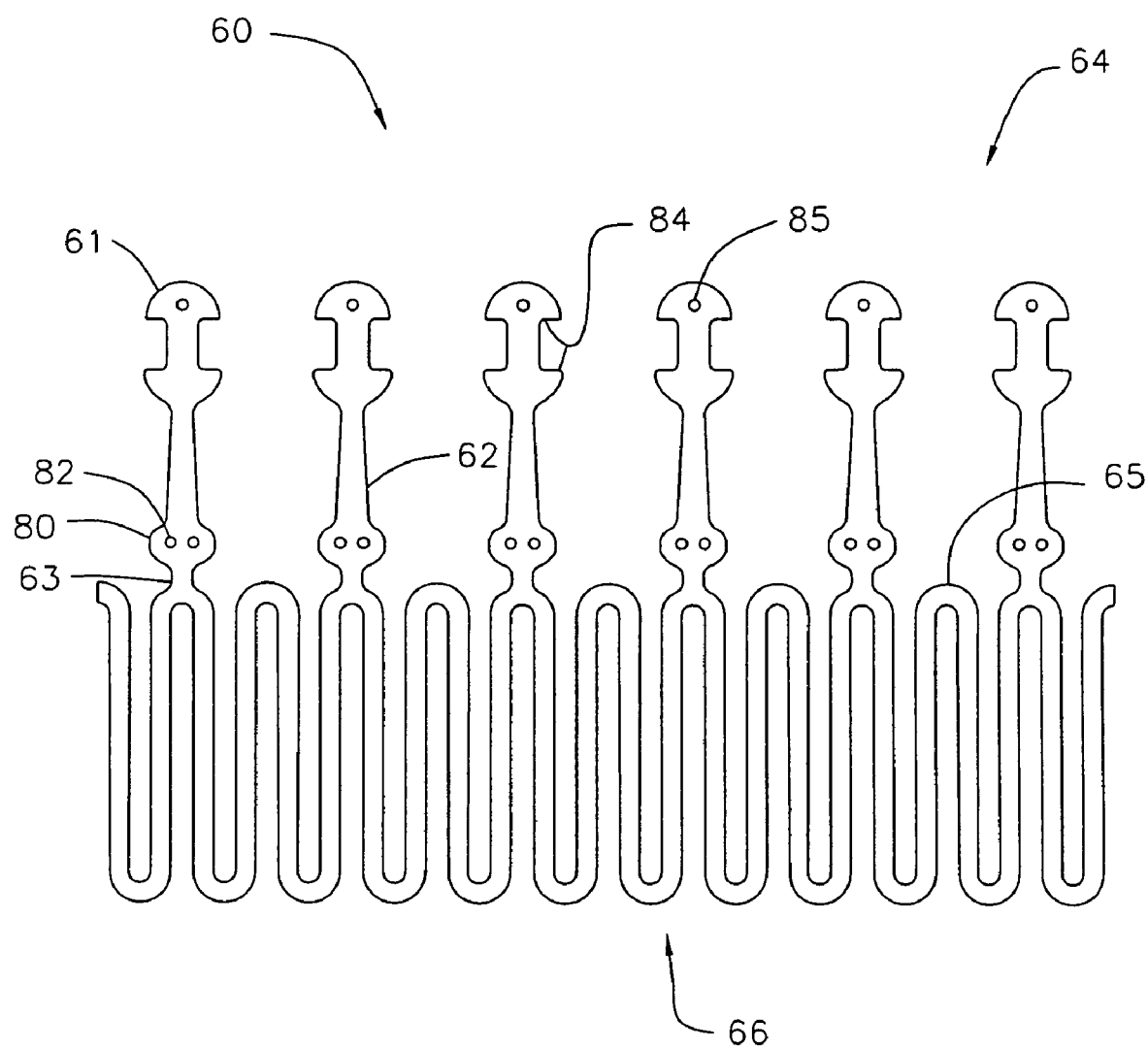
FIG. 3 shows a flat pattern of a component of the endovascular graft of FIG. 2.
Figure 4:
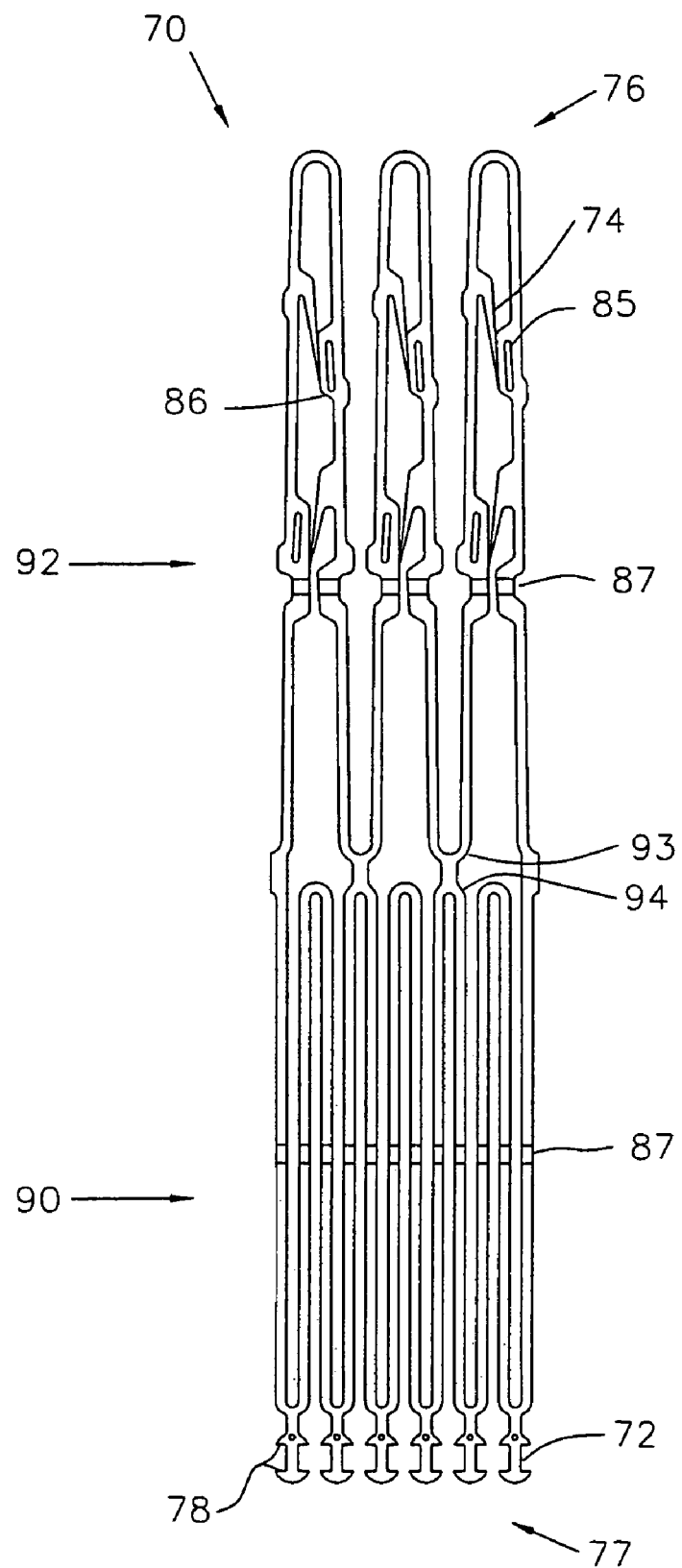
FIG. 4 shows a flat pattern of another component of the endovascular graft of FIG. 2.

FIG. 3 shows a detailed flat pattern view of the proximal connector member 60 shown in FIG. 2. Proximal connector member 60 comprises a distal end 66 and a proximal end 64 having twelve crowns or apices 65. Alternate proximal apices 65 comprise proximal connector member connector elements 62. These connector elements 62 each in turn comprises a proximal end 61, a distal end 63, and optional ears 80 disposed near distal end 63. Ears 80 provide for increased surface area on connector elements 62 to aid in maximizing the strength of the bond between connector element and graft proximal neck portion and further comprises one or more optional apertures 82 to further enhance such a bond as previously discussed. Opposing shoulder portions 84 may have rounded corners so to minimize their potential to snag, tear, or otherwise interfere with other components of the graft or the lumen in which it is deployed. Shoulder portions 84 also have one or more optional shoulder holes 85. These shoulder holes 85 are useful in helping to stabilize the proximal stent 70 and proximal connector member 60 device as they are coupled during assembly as discussed below in conjunction with FIG. 5A. As illustrated in FIGS. 4–5 and 6–7, two-stage proximal stent 70 has a proximal end 76 and a distal end 77 with proximal stent connector elements 72. Proximal stent connector elements 72 have opposing shoulder portions 78 that may mirror opposing shoulder portions 84 of proximal connector member connector elements 62.

Figure 6:
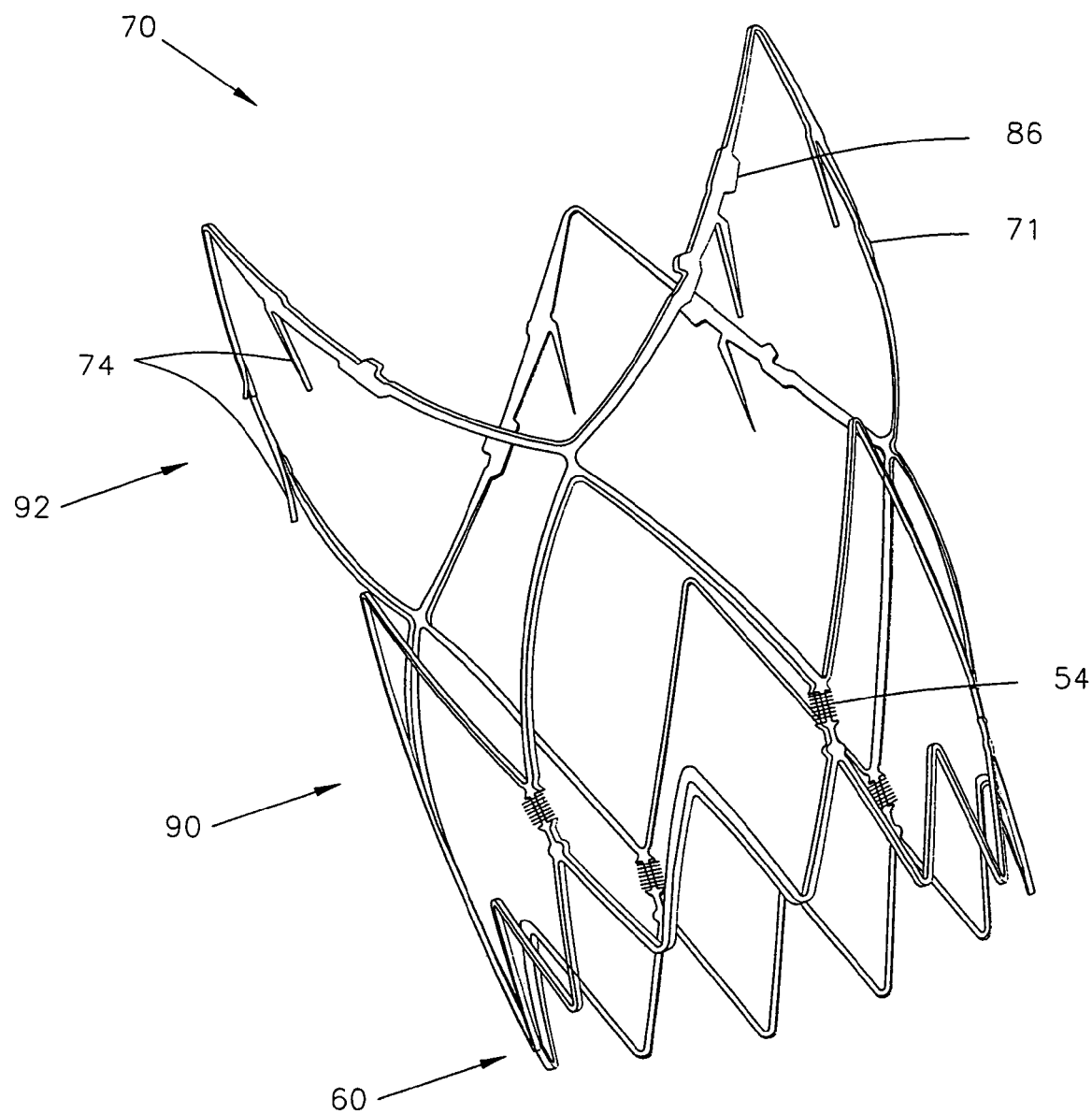
FIG. 6 is an enlarged view of a portion of an endovascular graft having features of an embodiment of the present invention.

Proximal stent 70 comprises struts 71, any one of which may further comprise one or more barbs 74. Optional barb tuck pads 86 near each barb serve to shield barbs 74 when graft 50 is in its reduced diameter delivery configuration. Struts 71 or tuck pads 86 may also contain an optional barb tuck slot 85 to help retain barbs 74 while graft 50 (and consequently proximal stent 70) is in its delivery configuration. Upon deployment of graft 50 as previously described with respect to the FIG. 1 embodiment, barbs 74 are released from barb tuck slots 85 and are placed in their operational, or deployed configuration, as shown in FIGS. 2 and 6. When so deployed in a patient vessel, proximal stent 70 is expanded, forcing barbs 74 at least partially into the vessel wall to emplace graft 50 therein and to resist fluid flow forces that might otherwise dislodge graft 50.

Proximal stent 70 also may comprise one or more sets of optional grooves 87 for housing device release bands as previously discussed.

Unlike proximal stent 40 of FIG. 1, however, proximal stent 70 is a two-stage component having a first, or six-crown region 90 and a second, or three-crown region 92. The first, or six-crown region 90 comprises a serpentine ring having six apices 94 (i.e., six distal and six proximal apices). Likewise, the second, or three-crown region 92 comprises a serpentine ring having three apices 93, the distal apices of which connect to every other proximal apex 94 of six-crown region 90. Note that proximal stent 70 is typically made from a single piece of material such that there are no joints or connections between each stage (such as a mechanical connection or a weld, etc.). However, other configurations in which two or more stages may be so joined or connected from separate parts or stents to form a single stent are possible; likewise, single-piece stents having more than two stages are also possible.

Proximal stent 70 may exhibit a greater outward radial force at three-crown region 92 than in six-crown region 90. Such a design is particularly useful in a clinical setting in which it is desired that such outward radial force be applied within a healthier section of vessel, more remote from the site of disease. Proximal stent 70 may accordingly perform the anchoring function within a portion of vessel that can accommodate such radial force.

Figures 5, 5A:
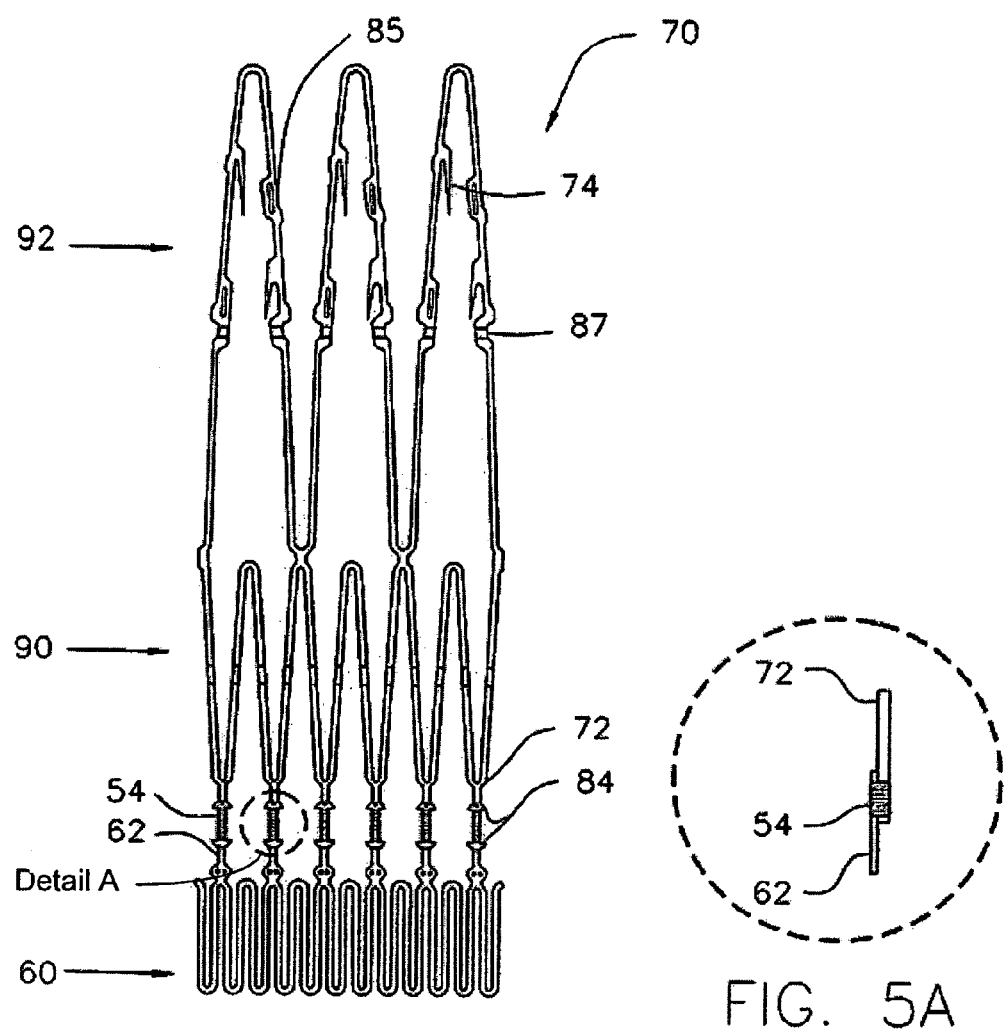
FIG. 5 shows a flat pattern of a portion of the endovascular graft of FIG. 2.
FIG. 5A is an enlarged side view of FIG. 5 at Detail A.

FIG. 5 is a flat pattern view of connector member 60 joined to proximal stent 70. For this embodiment, there is a relationship among the various apices 65, 93 and 94 of the connector member 60 and the two stages of proximal stent 70, respectively, in which there are twelve connector member apices 65, six apices 94 in the proximal stent first or six-crown region 90 and three apices 93 in the proximal stent second or three-crown region 92.

While the actual number of apices may vary as previously discussed, this more generally illustrates a useful convention for the present invention in which the relationship among the various apices may be described: for instance, if the number of connector member 60 apices 65 is denoted "n", "n/2" then denotes the number of proximal stent 70 first or six-crown region 90 apices 94 and "n/4" as the number of proximal stent 70 second or three-crown region 92 apices 93. Other useful embodiments include those in which there are "n" connector member apices, "n" proximal stent first region apices, and "n/2" proximal stent second region apices. These ratios may vary as appropriate; these particular sets of ratios are merely illustrative.

Note also in FIG. 5 that connector member connector elements 62 are coupled to proximal stent connector elements 72 via coupling members 54.

FIG. 5A is a side view of proximal stent connector element 72, connector member connector element 62, and coupling member 54. Coupling member 54 is a wire or similar element wrapped to form a coil around the overlapping connector member connector element 62 and proximal stent connector element 72 to mechanically join connector member 60 to proximal stent 70. Alternatively, any other suitable joining technique, such as welding, brazing, soldering, mechanical means, adhesive, etc. may be used to join these components of the graft 50. We have found, however, that mechanical means such as coupling member 54 is most useful in that it avoids problems presented by techniques such as welding, etc., where possible heat-affected zones some distance from the joint may deleteriously affect the microstructure of the stent/connector element material, especially when that material is nickel titanium, thus having a negative impact on the joint strength, fatigue life, and ultimately the integrity of graft 50.

Any suitable member may be used for coupling member 54 although we have found a wire or wire-like member having a circular cross-sectional shape to be useful (although any shape may be used). Optimally, the wire coupling member 54 may be formed of a suitable metal such as nickel, stainless steel, nickel-titanium, etc. The wire may have a diameter ranging from about 0.002 to about 0.006 inch; more specifically from about 0.003 to about 0.005 inch.

To secure the connector elements 62 and 72 to one another, coupling member 54 may be wound around the matched connector elements one or more times. We have found that providing enough windings to present a single layer of wire in which the windings are immediately adjacent one another from shoulder 78, 84 to shoulder 78, 84 provides sufficient strength and stiffness to the joint thus created without detracting from the low delivery profile afforded by the novel design of graft 50. Thus the number of optimal windings from graft to graft will vary but typically ranges from about 6 to about 18 windings in most applications. With coupling members 54 in place, connector member connector elements 62 and proximal stent connector elements 72 are securely coupled to one another. The features and advantages of coupling member 54 discussed herein may be utilized by any of the embodiments of the present invention herein discussed.

FIG. 6 is a perspective view of connector member 60 joined to proximal stent 70 in this way in their expanded, or deployed configuration. Graft body section 53 and other graft components are removed for clarity of illustration. Barbs 74 are shown in their deployed state, released from optional barb tuck pads 86.

Figure 7:
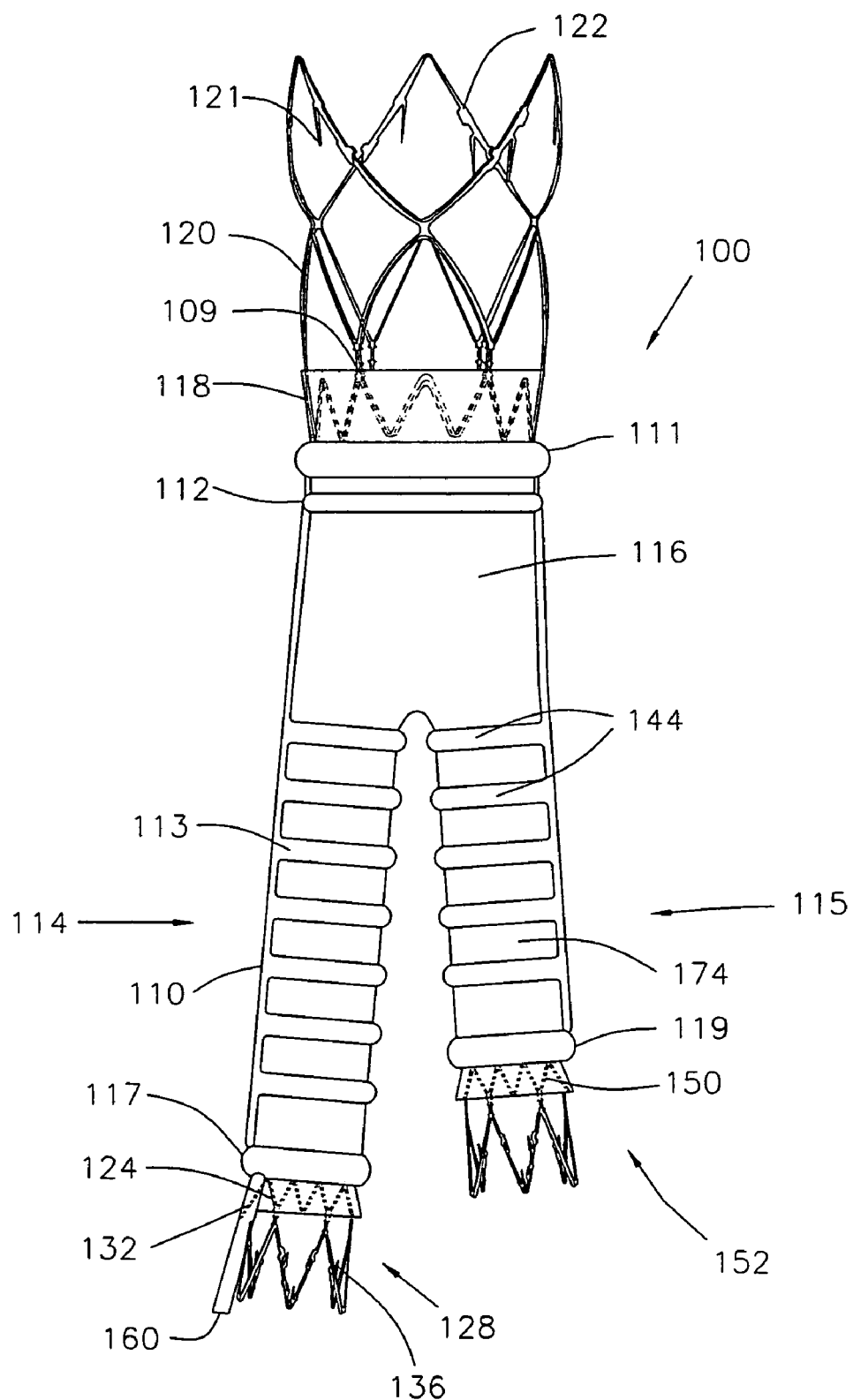
FIG. 7 shows a bifurcated endovascular graft according to embodiments of the present invention.

FIG. 7 illustrates another embodiment of the invention in the form of a bifurcated endovascular graft 100. A bifurcated device such as endovascular graft 100 may be utilized to repair a diseased lumen at or near a bifurcation within the vessel, such as, for example, in the case of an abdominal aortic aneurysm in which the aneurysm to be treated may extend into the anatomical bifurcation or even into one or both of the iliac arteries distal to the bifurcation. In the following discussion, the various features of the graft embodiments previously discussed may be used as necessary in the bifurcated graft 100 embodiment unless specifically mentioned otherwise.

Graft 100 comprises a first bifurcated portion 114, a second bifurcated portion 115 and main body portion 116. The size and angular orientation of the bifurcated portions 114 and 115, respectively, may vary—even between portion 114 and 115—to accommodate graft delivery system requirements and various clinical demands. For instance, each bifurcated portion or leg is shown in FIG. 7 to have a different length, but this is not necessary. First and second bifurcated portions 114 and 115 are generally configured to have an outer inflated diameter that is compatible with the inner diameter of a patient's iliac arteries. First and second bifurcated portions 114 and 115 may also be formed in a curved shape to better accommodate curved and even tortuous anatomies in some applications.

Together, main body portion 116 and first and second bifurcated portions 114, 115 form a continuous bifurcated lumen, similar to lumens 22 and 73, which is configured to confine a flow of fluid therethrough. And although not shown in FIG. 7, graft 100 does not have to have a second bifurcated portion 115, in which case the bifurcated lumen is formed between main body portion 116 and first bifurcated portion 114.

First and second bifurcated portions 114 and 115 each comprises a network of inflatable cuffs and channels as discussed with respect to the FIG. 2 embodiment, including inflatable channel 113. Channel 113 comprises one or more optional inflatable longitudinal channels 110 in fluid communication with one or more approximately parallel inflatable circumferential channels 144, all of which are in fluid communication with optional distal inflatable cuffs 117 and 119.

As with the embodiments previously discussed, the number of inflatable circumferential channels 144 may vary with the specific configuration of the graft as adapted to a given indication. Generally, however, the number of inflatable circumferential channels 144 per bifurcated portion may range from 1 to about 30, preferably about 10 to about 20. Similarly, the dimensions, spacing, angular orientation, etc. of circumferential inflatable channels 144 may vary as well.

For instance, the distance between and width of each circumferential inflatable channel 144 may vary along the length of the graft or may be constant. The pitch or inter-ring distance may range from about 2 to about 20 mm; specifically, it may range from about 3 to about 10 mm. Circumferential inflatable channels 144 are each typically between about 2 and about 4 mm wide, but may be from about 1 to about 8 mm wide. Each longitudinal channel 110 is typically from about 2 to about 4 mm wide, but may vary, together or independently, to be from about 1 to about 8 mm wide.

In the embodiment of FIG. 7, channel 113 forms a continuous cuff and channel network extending from first bifurcated portion 114 to main body portion 116 to second bifurcated portion 115. Accordingly, inflatable channel 113 fluidly connects into a network with proximal inflatable cuff 111, secondary proximal cuff 112, circumferential inflatable channels 144, optional distal inflatable cuff 117 and optional distal inflatable cuff 119. Note that longitudinal channels 110 extend proximally along main body portion 116 to be in fluid communication with cuffs 111 and 112.

In alternative embodiments of the graft of FIG. 7 as well as that of FIGS. 1 and 2, numerous other inflatable channel and cuff configurations are possible. The inflatable channel for instance may be disposed longitudinally, horizontally, in a helical fashion, or otherwise. One or more additional cuffs may be disposed on either or both bifurcated portions 114 and 115 as well as main body portion 116. In other embodiments, graft 100 may have compartmentalized channels and cuffs requiring multiple sites from which they are inflated and may use multiple inflation materials to optimize properties in each region.

Second bifurcated portion 115 may be of a similar construction to first bifurcated portion 114. In the FIG. 7 embodiment of graft 100, second bifurcated portion 115 is of a unitary, continuous construction with first bifurcated portion 114 and main body portion 116. Alternatively, first and second bifurcated portion 114 and 115 respectively may be singly or jointly formed separately from a main body portion and may be joined to the main body portion before deployment in the body passageway or in vivo after such deployment.

First and second bifurcated portions 114 and 115 may be generally cylindrical in shape when deployed, and will generally conform to the shape of a vessel interior within which they are deployed. Their length as measured from main body portion 116 may range from about 1 to about 10 cm or more. The nominal inflated outside diameter of the distal ends of the first and second bifurcated portions 114 and 115 at cuffs 117 and 119 may range from about 2 to about 30 mm, preferably from about 5 to about 20 mm.

Main body portion 116 comprises a proximal inflatable cuff 111 and an optional secondary proximal inflatable cuff 112 in fluid communication with one or more inflatable longitudinal channels 110. As with other embodiments, proximal cuff 111 serves primarily to seal graft 100 firmly against a lumen wall. Secondary proximal inflatable cuff 112 has been found to confer additional kink resistance on graft 100, particularly in those clinical applications in which the vessel in which the graft is deployed is highly angled or tortuous. The nominal inflated outside diameter of secondary proximal inflatable cuff 112 may range from about 10 to about 45 mm, preferably from about 15 to about 30 mm, while the nominal inflated outside diameter of proximal cuff 111 may range from about 10 to about 45 mm, preferably from about 16 to about 32 mm. Main body portion 116 may range in length from about 2 to about 10 cm; preferably from about 4 to about 8 cm.

Endovascular graft 100 further comprises a proximal connector member 118, proximal stent 120, and proximal neck portion 146 all of which may be similar to those components discussed above in reference to FIGS. 2–6. Coupling members (not shown) may join proximal stent 120 and proximal connector member 118 as discussed with respect to the embodiments of FIGS. 1–6. Proximal connector members and proximal stents as discussed in conjunction with the FIG. 1 embodiment are also possible for use in bifurcated graft 100.

In bifurcated embodiments of grafts having features of the invention which also have a biased proximal end that forms an inlet axis angle, the direction of the bias or angulation can be important with regard to achieving a proper fit between the graft and the morphology of the deployment site. Generally, the angular bias of the proximal end of the graft, proximal neck portion or proximal anchor can be in any direction. Preferably, the angular bias is in a direction and of a magnitude consistent with the mean angulation of the type of lesion (e.g. abdominal aortic aneurysm) intended for treatment with the graft.

As with proximal stent 70 of the embodiments shown in FIGS. 2 and 4–6, proximal stent 120 comprises barbs 121 which are oriented in a distal direction for reliable anchoring against the direction of pulsatile forces in vivo when the device is implanted in the abdominal aorta, for instance, to treat an abdominal aortic aneurysm.

One or both bifurcated portions 114 and/or 115 may further comprise a distal connector member 124 and/or 150, a distal stent 128, and a distal neck portion 154. The embodiment of FIG. 7 has distal connector member 124 and distal stent 128 disposed at the distal ends of each of first and second bifurcated portions 114 and 115, respectively. Distal connector member 124 and distal stent 128 are shown in greater detail in FIGS. 8 and 9.

Figure 8:
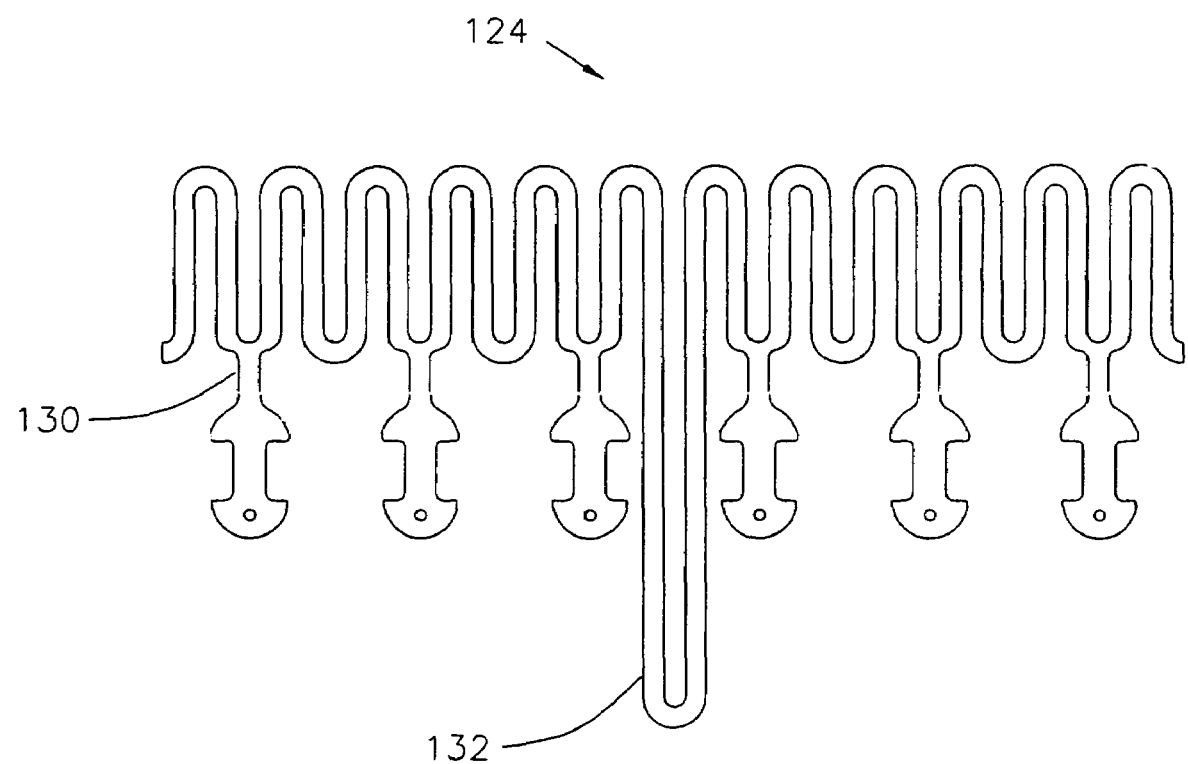
FIG. 8 shows a flat pattern of yet another component of the endovascular graft of FIG. 2.

As discussed with respect to the FIG. 2 embodiment and as shown more clearly in FIG. 8, distal connector member 124 disposed at or near first bifurcated portion 114 comprises distal connector member connector elements 130 and an optional fill-port bridge 132. Fill-port bridge 132 serves to prevent interference by distal connector member 124 with the manufacture of graft 100 and with the injection of an inflation medium, while preserving the continuous ring structure of distal connector member 124.

Inflatable channels 113 (and other inflatable members of the invention) are in communication with a fill port 160 through distal inflatable cuff 117. Fill port 160 may be disposed alternatively on second bifurcated portion 115 or graft main body portion 116, and more than one fill port may be used. Fill port 160 is configured to accept a pressurized source of fluid (gas and/or liquid), particles, gel or combination thereof as previously discussed.

Figure 9:
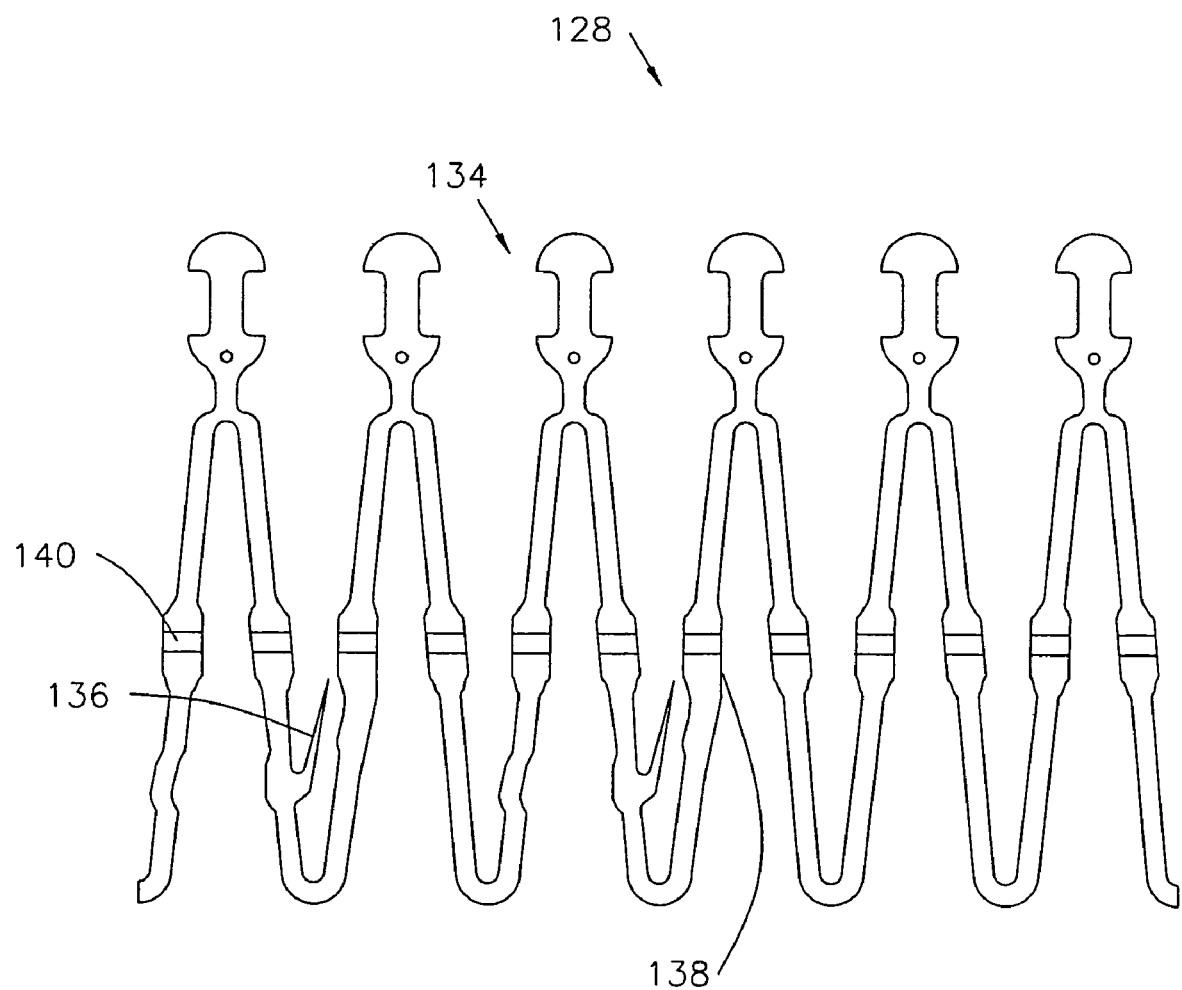
FIG. 9 shows a flat pattern of another component of the endovascular graft of FIG. 2.

As discussed with respect to the FIG. 2 embodiment, FIG. 9 details a flat pattern of distal stent 128, which includes distal stent connector elements 134. Distal connector member connector elements 130 are configured to be coupled with distal stent connector elements 134 via coupling members (not shown) similar to those discussed with respect to the FIGS. 1–6 embodiments. Distal stent 128 comprises one or more optional distal stent barbs 136, one or more optional distal stent barb tuck pads 138 and one or more optional distal stent barb tuck slots 140, each of which functions in a similar fashion to the corresponding features of embodiments discussed above. Distal stent barbs 136 are oriented proximally, opposite the direction of orientation of barbs 121, to accommodate the environment often found in the iliac arteries that can cause the bifurcated portions 114 and 115 to migrate proximally in vivo. Note that only two distal stent barbs 136 are shown in FIG. 9 for the purposes of clarity of illustration despite a larger number being depicted in the FIG. 7 embodiment of the present invention. It is understood that all embodiments of the present invention includes proximal and distal stents each of which may optionally comprise one, two, or any number of barbs.

The optional distal connector member 150, disposed in the FIG. 7 embodiment at or near distal end 152 of second bifurcated portion 115, has a structure similar to that of first bifurcated portion 114, with the exception of the absence of fill-port bridge 132. Other embodiments of the invention include bifurcated grafts in which the distal connector member 150 includes a fill-port bridge.

FIGS. 10–13 illustrate additional features of the present invention that may be used in any of the various stents and connector rings of the present invention, in any combination.

Figure 10:
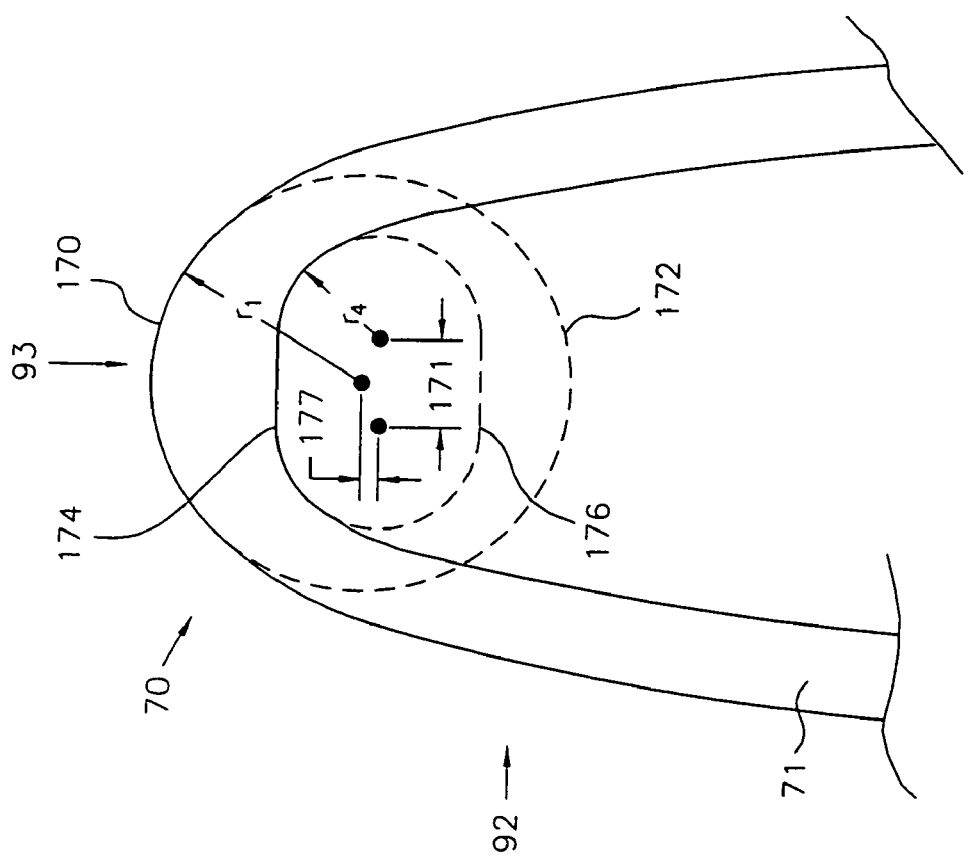
FIG. 10 shows detail of a stent apex detail that comprises offset circular and elliptical radii.

Turning to FIG. 10, a simplified detail of a proximal apex 93 of the second or three-crown region 92 of proximal stent 70 is shown. An outer surface 170 of apex 93 takes on a circular radius of curvature as defined by circle 172 having a radius $r_1$. An inner surface 174 of the stent strut apex 93 takes on an elliptical shape as shown by ellipse 176. In the configuration of FIG. 10, circle 172 and ellipse 176 offset as shown by reference numeral 177; however, they may share a common center. Radius $r_4$ shown at one of the foci of ellipse 176; the foci are shown as separated by a distance 171 in FIG. 10.

We have found that for the NiTi stents used in the present invention, such a configuration provides for a more diffuse strain distribution in the stent and reduces the peak strains experienced during assembly and in vivo, while also allowing for a smaller delivery profile as compared to other configurations, particularly in the proximal apex 93 of the second or three-crown region 92 of proximal stent 70. However, the stent apex configuration of FIG. 10 may be used in any other stent or connector member apex described herein, and may be used for components comprising material other than NiTi.

In the example of FIG. 10 wherein proximal apex 93 of the second or three-crown region 92, we have found that for NiTi components radius $r_1$ of between about 0.030 and about 0.070 inch; specifically about 0.050 inch is useful, while an offset 171 of between about zero and about 0.050 inch; specifically about 0.0025 inch, is effective. A radius $r_4$ of between about 0.010 and about 0.030 inch; specifically about 0.020 inch, is useful as well.

Figure 11:
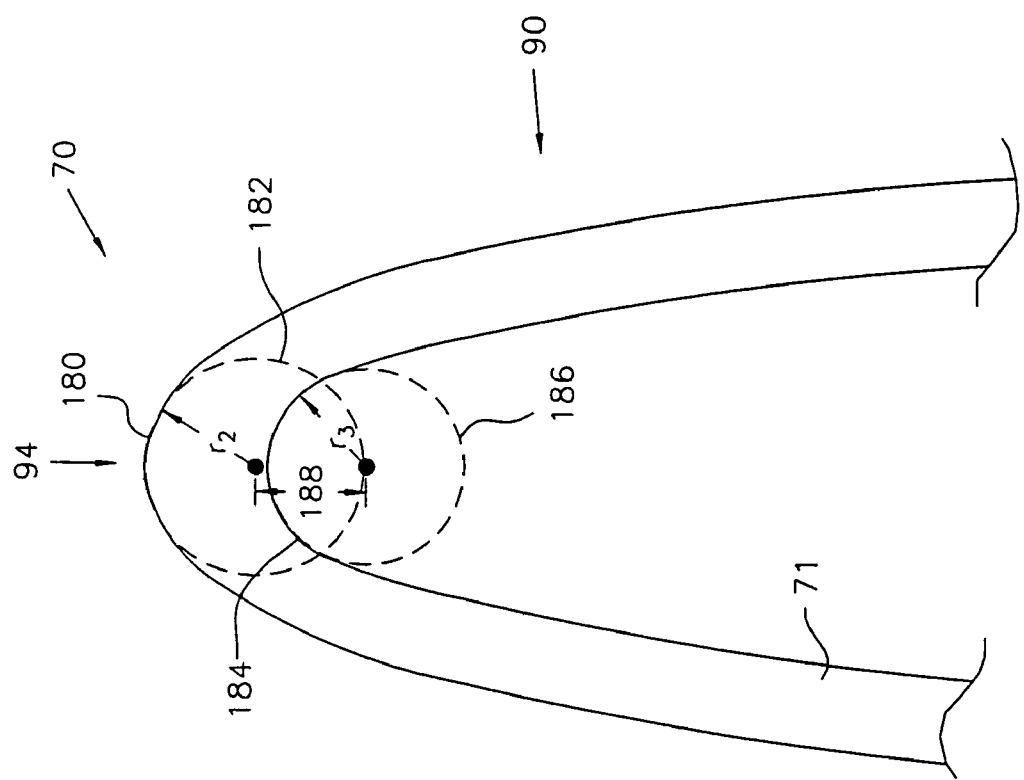
FIG. 11 shows detail of a stent apex detail that comprises offset circular radii.

FIG. 11 details an alternative offset circular apex configuration. Here, a simplified detail of proximal apex 94 in the first or six-crown region 90 of proximal stent 70 is shown (without a transition region to the second or three-crown stent region as seen in, e.g., FIG. 4 for clarity of illustration). An outer surface 180 of apex 94 takes on a circular radius of curvature as defined by circle 182 having a radius $r_2$. An inner surface 184 of apex 94 takes on a circular radius of curvature defined by circle 186 having a radius $r_3$. Radius $r_2$ may be equal to or greater than radius $r_3$ and be within the scope of the present invention. The centers of circles 182 and 186 are offset from each other as indicated by reference numeral 188 in FIG. 11. This offset 188 may be equal to, greater than, or less than the width of the strut 71 in the region of apex 94.

We have found that when NiTi is used for the stents and connector members of the present invention, such a configuration is effective in distributing the peak strains experienced in the stent from the apex 94 to stent strut 71 as compared to other configurations, particularly in the proximal apex 94 of the first or six-crown region 90 of proximal stent 70. However, the offset circular apex configuration of FIG. 11 may be used in any other stent or connector member apex described herein, and may be used for components comprising material other than NiTi.

When used in the proximal apex 94 of the proximal stent first or six-crown region 90, we have found offset values ranging from about zero to about 0.030 inch; particular about 0.020 inch, to be effective in NiTi stents having expanded, or deployed diameters ranging from about 16 to about 26 mm. We have also found effective a configuration in which radius $r_2$ ranges from about 0.020 to about 0.040 inch; more particularly about 0.035 inch, and in which radius $r_3$ ranges from about 0.005 to about 0.020 inch; in particular about 0.010 inch.

Optional taper or tapers may be incorporated into the struts 41 and 71 of the various stent embodiments of the present invention as well as the various proximal and distal connector members. In general, incorporating one or more tapers into the struts on both proximal and distal stents provide greater space in the tapered region to accommodate alternative features such as barbs and tuck pads. It allows for a smaller deployment profile when the component is in a radially collapsed delivery configuration. We have found that when configuring the various stents and connector elements of the present invention into this reduced diameter delivery profile, the stents experience a large degree of bending strain that is often poorly or locally distributed. Tapering certain stent struts in particular locations helps to distribute this strain more evenly throughout the stent or connector member and to manage the peak strains. The examples of FIGS. 12 and 13 are now introduced and discussed below.

Figure 12:
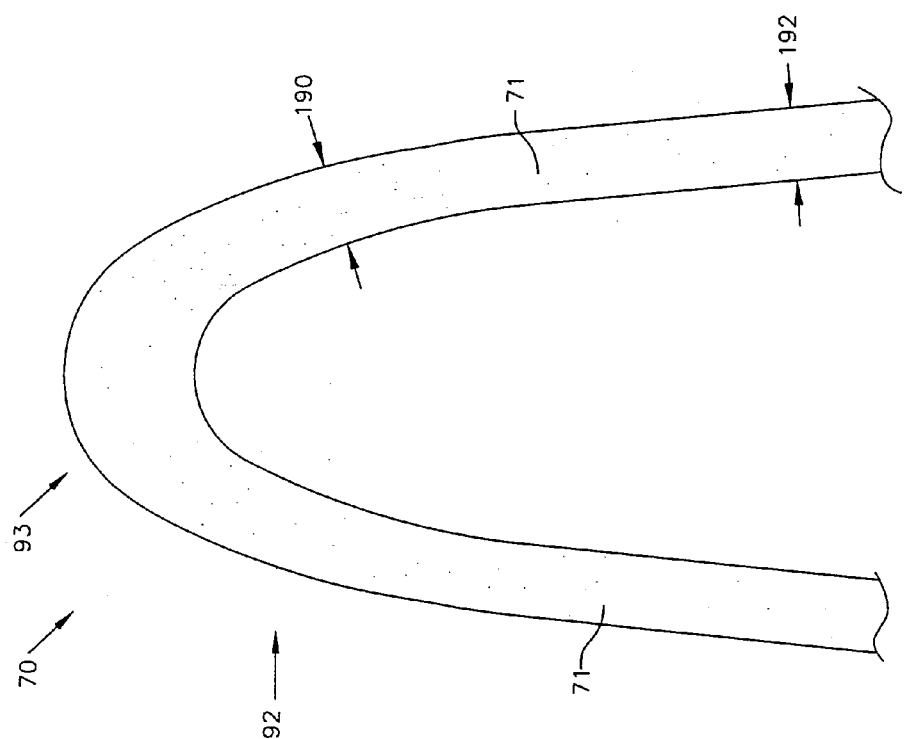
FIG. 12 shows detail of a stent section comprising a tapered strut section.

In FIG. 12, a simplified section of the second or three-crown region 92 of proximal stent 70 is depicted in which the stent struts 71 taper from a maximum width 190 (which may or may not equal a width of strut 71 in region of apex 93) to a minimum width 192. The optional taper, expressed as the ratio of the maximum width 190 to the minimum width 192, may vary widely depending on the particular region of the stent or connector member, the material used, and other factors. Taper ratios ranging from 1 to about 10 or greater are within the scope of the present invention. It is also within the scope of the present invention for the stent struts 71 to exhibit no taper.

For example, in a proximal stent 70 three-crown region 92 made from NiTi, we have found effective a maximum strut width 190 ranging from about 0.016 to about 0.032 inch; particularly from about 0.022 and about 0.028 inch, and a minimum strut width 192 of between about 0.010 and about 0.026 inch; particularly from about 0.012 and about 0.022 inch. The optional tapered strut feature described herein and shown in FIG. 12 may be used in any other stent or connector member described herein, and may be used for components comprising material other than NiTi.

Figure 13:
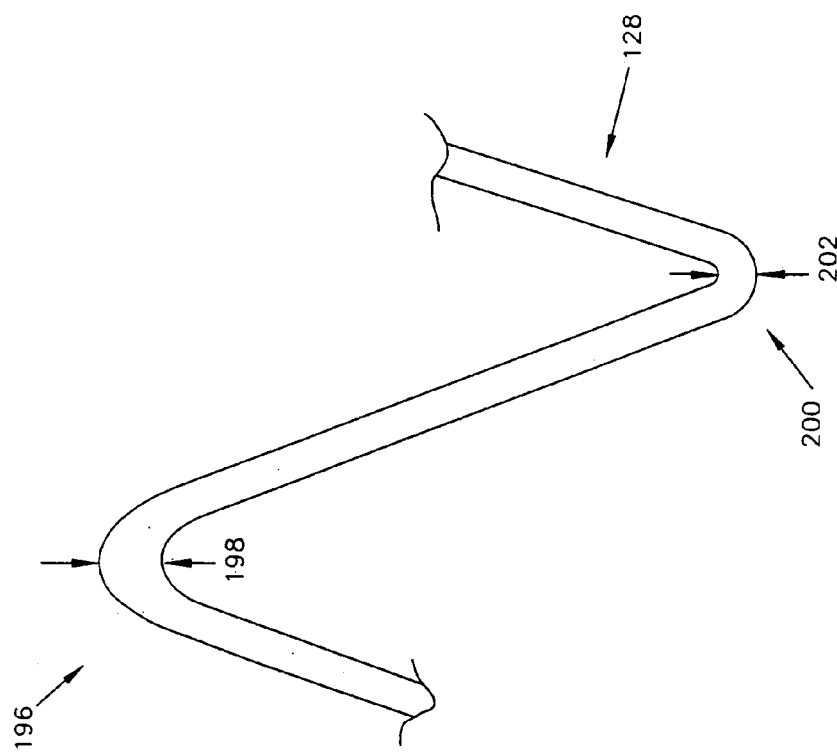
FIG. 13 shows detail of a stent section comprising another configuration for a tapered strut section.

Turning now to FIG. 13, a simplified section of distal stent 128 is shown as an example of optional tapering that results in asymmetric crowns. In this example, distal stent 128 comprises a distal apex or crown 196 exhibiting a width 198 and a proximal apex or crown (with connector element 134 removed for clarity of illustration) 200 exhibiting a smaller width 202. It is within the scope of the present invention for width 198 and width 202 to be equal.

We have found that, especially for the distal stents of the present invention, an asymmetric crown in which the distal apex 200 has a smaller strut width than that of the proximal apex 196 results in a difference in the expansion force exerted between each of the proximal and distal apices. When deployed in a diseased lumen or vessel, the proximal apices of such a stent having this configuration will tend to exert a smaller expansion force near the graft seal zone, reducing the potential for such a stent to cause trauma to tissue in the seal zone near the cuffs (where weaker, more diseased tissue tends to reside). Such a configuration also facilitates a consistent, safe and predictable deployment when the component moves from a reduced diameter delivery profile to an expanded treatment profile. Finally, such a taper reduces the flare exhibited by the distal apex 200; this in turn provides for a smaller distal stent delivery profile when the distal stent is in a reduced-diameter configuration. Taper ratios (defined in the same manner above as the ratio between width 198 and width 202) ranging from 1 to about 10 or higher are within the scope of the present invention.

For distal stent 128 comprising NiTi, we have found that a width 202 ranging from about 0.010 to about 0.026 inch; specifically from about 0.012 and about 0.024 inch to be useful, and we have found a width 198 ranging from about 0.016 to about 0.032 inch; specifically from about 0.017 to about 0.028 inch to be useful.

Of course, the various types of offset radii and combinations of elliptical and circular apex radii may be used to effect these tapers and ratios so to further cause the desired behavior during assembly into a reduced-diameter delivery configuration, effective delivery and performance in vivo.

Useful inflation media generally include those formed by the mixing of multiple components and that have a cure time ranging from a few minutes to tens of minutes, preferably from about three and about twenty minutes. Such a material should be biocompatible, exhibit long-term stability (preferably on the order of at least ten years in vivo), pose as little an embolic risk as possible, and exhibit adequate mechanical properties, both pre- and post-cure, suitable for service in the graft of the present invention in vivo. For instance, such a material should have a relatively low viscosity before solidification or curing to facilitate the graft cuff and channel fill process. A desirable post-cure elastic modulus of such an inflation medium is from about 50 to about 400 psi—balancing the need for the filled graft to form an adequate seal in vivo while maintaining clinically relevant kink resistance of the graft. The inflation media ideally should be radiopaque, both acute and chronic, although this is not absolutely necessary.

Details of compositions suitable for use as an inflation medium in the present invention are described in greater detail in U.S. patent application Ser. No. 09/496,231 to Hubbell et al., filed Feb. 1, 2000 and entitled "Biomaterials Formed by Nucleophilic Addition Reaction to Conjugated Unsaturated Groups" and U.S. patent application Ser. No. 09/586,937 to Hubbell et al., filed Jun. 2, 2000 and entitled "Conjugate Addition Reactions for the Controlled Delivery of Pharmaceutically Active Compounds". The entirety of each of these patent applications is hereby incorporated herein by reference.

We have found one particular three-component medium formed by the Michael addition process to be particularly useful in serving as an inflation medium for the present invention. This medium comprises:

(1) polyethylene glycol diacrylate (PEGDA), present in a proportion ranging from about 50 to about 55 weight percent; specifically in a proportion of about 52 weight percent;

(2) pentaerthyritol tetra 3 (mercaptopropionate) (QT) present in a proportion ranging from about 22 to about 27 weight percent;
specifically in a proportion of about 24 weight percent, and (3) glycylglycine buffer present in a proportion ranging from about 22 to about 27 weight percent; specifically in a proportion of about 24 weight percent.

Variations of these components and other formulations as described in copending U.S. patent application Ser. Nos. 09/496,231 and 09/586,937, both to Hubbell et al., may be used as appropriate. In addition, we have found PEGDA having a molecular weight ranging from about 350 to about 850 to be useful; PEGDA having a molecular weight ranging from about 440 to about 560 are particularly useful.

Radiopaque materials as previously discussed may be added to this 3-component system. We have found that adding radiopacifiers such as barium sulfate, tantalum powder, and soluble materials such as iodine compounds to the glycylglycine buffer is useful.

We have found that triethanolamine in phosphate-buffered saline may be used as an alternative to glycylglycine buffer as the third component described above to form an alternative curable gel suitable for use in embodiments of the present invention.

An alternative to these three-component systems is a gel made via polymer precipitation from biocompatible solvents. Examples of such suitable polymers include ethylene vinyl alcohol and cellulose acetate. Examples of such suitable biocompatible solvents include dimethylsulfoxide (DMSO), n-methyl pyrrolidone (NMP) and others. Such polymers and solvents may be used in various combinations as appropriate.

Alternatively, various siloxanes may be used as inflation gels. Examples include hydrophilic siloxanes and polyvinyl siloxanes (such as STAR-VPS from Danville Materials of San Ramon, Calif. and various silicone products such as those manufactured by NuSil, Inc. of Santa Barbara, Calif.).

Other gel systems useful as an inflation medium or material for the present invention include phase change systems that gel upon heating or To cooling from their initial liquid or thixotropic state. For example, materials such as n-isopropyl-polyacrylimide (NIPAM), BASF F-127 pluronic polyoxyamer, and polyethylene glycol (PEG) chemistries having molecular weights ranging between about 500 and about 1,200 are suitable.

Effective gels may also comprise thixotropic materials that undergo sufficient shear-thinning so that they may be readily injected through a conduit such as a delivery catheter but yet still are able to become substantially gel-like at zero or low shear rates when present in the various channels and cuffs of the present invention.

In the case of the three-component PEDGA-QT-glycylglycine formulation described above, a careful preparation and delivery protocol should be followed to ensure proper mixing, delivery, and ultimately clinical efficacy. Each of the three components is typically packaged separately in sterile containers such as syringes until the appropriate time for deploying the endovascular graft. The QT and buffer (typically glycylglycine) are first continuously and thoroughly mixed, typically between their respective syringes for approximately two minutes. PEGDA is then mixed thoroughly with the resulting two-component mixture for approximately three minutes. This resulting three-component mixture is then ready for introduction into the graft body section as it will cure into a gel having the desired properties within the next several minutes. Cure times may be tailored by adjusting the formulations, mixing protocol, and other variables according to the requirements of the clinical setting. Details of suitable delivery protocols for these materials are discussed in copending U.S. patent application Ser. No. 09/917,371 to Chobotov et al.

We have found the post-cure mechanical properties of these gels to be highly tailorable without significant changes to the formulation. For instance, these gels may exhibit moduli of elasticity ranging from tens of psi to several hundred psi; the formulation described above exhibits moduli ranging from about 175 to about 250 psi with an elongation to failure ranging from about 30 to about 50 percent.

Notably, we have found it helpful to add an inert biocompatible material to the inflation material. In particular, we have found that adding a fluid such as saline to the PEGDA-QT-glycylglycine formulation (typically after it has been mixed but before significant curing takes place) lowers the viscosity of the formulation and results in greater ease when injecting the formulation into the graft body section network of inflatable cuffs and channels without sacrificing the desired physical, chemical, and mechanical properties of the formulation or its clinical efficacy. In the appropriate volume percentages, adding materials such as saline may also reduce the potential for the inflation material such as PEGDA-QT-glycylglycine to pose an embolic risk in case of spillage or leakage. Saline concentrations as a volume percentage of the final saline/three-component formulation combination may range from zero to as high as sixty percent or more; to particularly suitable are saline concentrations ranging from about twenty to about forty percent. We have found a saline volume concentration of about thirty percent to be most suitable. Alternatives to saline may include biocompatible liquids, including buffers such as glycylglycine.

In more general terms, it is desirable to use an inflation medium in which each of its components is biocompatible and soluble in blood. A biocompatible inflation medium is desirable so to manage any toxicity risk in the case the inflation medium were inadvertently released into the patient's vasculature. A soluble inflation medium is desirable so to manage any embolism risk if released into the vasculature. Such an inflation medium should not disperse nor gel or solidify if spilled into flowing blood before curing. In the event of a spill, the normal blood flow would then rapidly disperse the components and their concentration would fall below the level required for crosslinking and formation of a solid. These components would then be eliminated by the body through standard pathways without posing an embolic risk to the patient. Among the many possibilities of an inflation medium example in which all of the components are soluble in blood is the combination polyethylene glycol diacrylate, a thiolated polyethyleneamine, and a buffer.

As previously discussed, more than one type of inflation medium, or more than one variant of a single type of inflation medium may be used in a single graft to optimize the graft properties in the region in which it is disposed.

For example, in the proximal and distal cuffs of the various embodiments of the present invention, the inflation material serves as a conformable sealing medium to provide a seal against the lumen wall. Desirable mechanical characteristics for the inflation medium in the proximal and distal cuffs would therefore include a low shear strength so to enable the cuff to deform around any luminal irregularities (such as calcified plaque asperities) and to conform to the luminal profile, as well as a high volumetric compressibility to allow the fill material to expand the cuffs as needed to accommodate any late lumen dilatation and maintain a seal.

In the channel or channels, by contrast, the inflation medium serves primarily to provide structural support to the lumen within which the graft is placed and kink resistance to the graft. Desirable mechanical characteristics for the inflation medium in the channel or channels therefore includes a high shear strength, to prevent inelastic deformation of a channel or channel segment due to external compression forces from the vessel or lumen (due, for example, to neointimal hyperproliferation) and low volumetric compressibility to provide stable support for adjacent channels or channel segments that may be in compressive contact with each other, thereby providing kink resistance to the graft.

Given these contrasting requirements, it may be useful to have different inflation materials fill different portions of the graft, such as one inflation medium for the proximal and distal cuffs and a second in the channel or channels.

In the various embodiments of the present invention, it is desirable that the inflation medium be visible through the use of techniques such as fluoroscopy during the time of deployment in which the graft cuffs and channels are being filled with the inflation medium. Such visibility allows the clinician to verify that the cuffs and channels are filling correctly and to adjust the filling procedure if they are not. It also provides an opportunity to detect any leakage or otherwise undesirable flow of inflation material out of the graft so that injection may be stopped, thereby minimizing the amount of leaked inflation material.

After the graft has been deployed into a patient, it is desirable that the graft be visible through the use of follow-up imaging techniques such as computed tomography (CT) and the like. However, the inflation material at this point in time is ideally not so radiopaque that it produces a dense CT image as such an image could potentially mask clinically significant endoleaks that would be visualized by opacifying the blood with a contrast agent.

Balancing these two objectives is difficult, however, since CT techniques are much more sensitive in detecting small amounts of radiopaque matter than are fluoroscopy techniques. One solution is to use an inflation medium that becomes less radiopaque over time, such as for example by using a blend of radiopaque materials in which one or more will diffuse out of the inflation medium over time, thereby reducing the inflation medium's radiopacity. For instance, a blend of a soluble contrast agent such as an iodinated aqueous solution and an insoluble contrast agent such as barium sulfate may serve this purpose. The soluble contrast agent will diffuse through the graft body section pores some time after the graft has been implanted, resulting in a progressive decrease in radiopacity of the inflation material over time. A fill material radiopacifier prepared from a combination of about two percent barium sulfate (by weight) and about 20 percent iodinated contrast solution (by weight) is useful in this capacity.

While particular forms of the invention have been illustrated and described, it will be apparent that various modifications can be made without departing from the spirit and scope of the invention.

We claim:

1. A radially expandable stent comprising:
   a first portion that comprises a serpentine ring that comprises 2n interconnected struts, wherein the interconnected struts define n proximal apices and n distal apices;
   a second portion that comprises a serpentine ring that comprises n interconnected struts, wherein the interconnected struts define n/2 proximal apices and n/2 distal apices,
   wherein n/2 of the n proximal apices of the first portion are integral with the n/2 distal apices of the second portion;
   a barb integrally formed on every other strut in the second portion;
   a tuck pad integrally formed in the struts in the second portion that are adjacent the struts that comprise the barb; and
   connector elements integrally formed with the n distal apices of the first portion.

2. The radially expandable stent of claim 1 further comprising a connector member coupled to the connector elements of the first portion.

3. The radially expandable stent of claim 2 wherein the connector member comprises a serpentine ring.

4. The radially expandable stent of claim 3 wherein the serpentine ring connector member comprises 2n interconnected struts that define n proximal apices and n distal apices.

5. The radially expandable stent of claim 4 wherein the n proximal apices of the connector member comprise n integral connector member connector elements.

6. The radially expandable stent of claim 5 wherein the n connector elements of the connector member are coupled to the n connector elements of the first portion via coupling members.

7. The radially expandable stent of claim 6 wherein the coupling members comprise wire or coil wrapped around the connector elements of the connector member and the connector elements of the first portion.

8. The radially expandable stent of claim 1 wherein at least one of the first and second portion comprises a set of grooves that are configured to receive release bands.

9. The radially expandable stent of claim 1 wherein a width of the struts are tapered between the proximal apices and distal apices.

10. The radially expandable stent of claim 9 wherein the struts have a maximum strut width at the proximal apices or distal apices, and a minimum strut width between the proximal apices and the distal apices.

11. The radially expandable stent of claim 10 wherein a ratio of the maximum strut width to minimum strut width is between about 1:1 and about 10:1.

12. The radially expandable stent of claim 1 wherein the one or more barbs have a length from about 1 to about 5 mm.

13. The radially expandable stent of claim 1 wherein the one or more barbs have a length from about 2 to about 4 mm.

14. The radially expandable stent of claim 1 wherein the radially expandable stent is self-expanding.

15. The radially expandable stent of claim 1 wherein the proximal apices of at least one of the first portion and second portion comprise a curved outer surface and a curved inner surface,
   wherein both the inner and outer surfaces of the apices comprise a circular radius of curvature.

16. The radially expandable stent of claim 15 wherein the circular radii of curvature comprise a common center point.

17. The radially expandable stent of claim 15 wherein the circular radii of curvature comprise center points that are offset.

18. The radially expandable stent of claim 1 wherein the one or more barbs project radially outward from a longitudinal axis of a strut in the radially expandable stent and at an elevation angle between about 10 degrees to about 45 degrees.

19. The radially expandable stent of claim 1 wherein the one or more barbs are laterally biased in a plane that is orthogonal to a plane in which the barb radial angle is formed to form a barb kick angle.

* * * * *